(12) United States Patent
Rimando et al.

(10) Patent No.: US 8,426,369 B2
(45) Date of Patent: Apr. 23, 2013

(54) PREVENTION AND TREATMENT OF COLON CANCER

(75) Inventors: Agnes M. Rimando, Oxford, MS (US); Nanjoo Suh, Bridgewater, NJ (US); Cassia Suemi Mizuno, Oxford, MS (US); Bandaru S. Reddy, Bridgewater, NJ (US); Subhashini Reddy, legal representative, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 659 days.

(21) Appl. No.: 12/518,271

(22) PCT Filed: Dec. 7, 2007

(86) PCT No.: PCT/US2007/086888
§ 371 (c)(1),
(2), (4) Date: May 4, 2010

(87) PCT Pub. No.: WO2008/070872
PCT Pub. Date: Jun. 12, 2008

(65) Prior Publication Data
US 2012/0178704 A1 Jul. 12, 2012

Related U.S. Application Data

(60) Provisional application No. 60/873,343, filed on Dec. 7, 2006, provisional application No. 60/991,549, filed on Nov. 30, 2007.

(51) Int. Cl.
*A61K 31/70* (2006.01)
*A61K 31/185* (2006.01)
*C07H 1/00* (2006.01)
*C07C 39/10* (2006.01)

(52) U.S. Cl.
USPC ............. 514/23; 514/25; 514/576; 536/1.11; 536/4.1; 568/765

(58) Field of Classification Search ................. 536/1.11, 536/4.1; 568/765; 514/23, 25, 576
See application file for complete search history.

(56) References Cited

U.S. PATENT DOCUMENTS

| | | | |
|---|---|---|---|
| 6,528,053 B1 * | 3/2003 | Yegorova | 424/94.2 |
| 2002/0058707 A1 | 5/2002 | Hopp et al. | |
| 2004/0259938 A1 | 12/2004 | Nag et al. | |
| 2005/0240062 A1 | 10/2005 | Pettit et al. | |
| 2006/0035984 A1 | 2/2006 | Docherty | |
| 2006/0057231 A1 | 3/2006 | Rimando et al. | |

OTHER PUBLICATIONS

Rimando et al, "Cancer Chemoprotective and Antioxidant Activities of Pterstilbene, A Naturally Occurring Analogue of Resveratrol", Journal of Agricultural and Food Chemistry, 2002, vol. 50, pp. 3453-3457.*

Rimando, et al., "Resveratrol, pterostilbene, and piceatannol in vaccinium berries" J. Agric. Food Chem. (2004); vol. 52(15), pp. 4713-4719, Abstract Only.

* cited by examiner

*Primary Examiner* — Elli Peselev
(74) *Attorney, Agent, or Firm* — Fox Rothschild LLP

(57) ABSTRACT

Stilbene compounds for the prevention and treatment of colon cancer or colon inflammation and methods of using same are provided.

18 Claims, 14 Drawing Sheets

Pterostilbene and analogs

| Code | Name from USDA | Molecular Wt (g/mol) |
|---|---|---|
| ARS 1 | AR-CM-1-14-T-A | 285.29 |
| ARS 2 | AR-CM-1-14-C-A | 285.29 |
| ARS 3 | AR-CM-1-24-T-A | 255.31 |
| ARS 4 | AR-CM-1-42-A | 255.31 |
| ARS 5 | AR-CM-1-12-T-A | 298.33 |
| ARS 6 | AR-CM-1-12-C-A | 298.33 |
| ARS 7 | AR-CM-1-13-T-A | 284.31 |
| ARS 8 | AR-CM-1-32-T-A | 270.32 |
| ARS 9 | AR-CM-1-32-C-A | 270.32 |
| ARS 10 | AR-CM-1-37-A | 242.27 |
| ARS 11 | AR-CM-1-43-A | 258.31 |
| ARS 12 | AR-CM-1-54-T-A | 242.27 |
| ARS 13 | AR-CM-1-54-C-A | 242.27 |
| ARS 14 | AR-CM-1-23-A | 336.38 |
| ARS 15 | AR-CM-P-A (pterostilbene) | 256.3 |
| ARS 16 | AR-CM-R-A (resveratrol) | 228.24 |
| ARS 17 | AR-CM-1-51-C-A | 284.31 |

Fig. 5

PREVENTION AND TREATMENT OF COLON CANCER

RELATION TO PRIOR APPLICATIONS

This application is a National Stage filing under 35 U.S.C. §371(c) of International Application PCT/US07/086888 filed on Dec. 7, 2007. PCT/US07/086888 claims priority benefit under 35 U.S.C. §119(e) to U.S. Provisional Application Nos. 60/873,343 filed on Dec. 7, 2006 and 60/991,549 filed on Nov. 30, 2007. The disclosures of all three applications are incorporated herein by reference.

GOVERNMENTAL SUPPORT

The research of the subject matter of the instant application was supported by NIH grant NIH/NCI K22 CA99990.

FIELD OF THE INVENTION

This invention is most closely related to the prevention and treatment of colon cancer.

BACKGROUND

Stilbenes, such as resveratrol and pterostilbene, are a subset of naturally occurring phenolic compounds known to have diverse pharmacological activities including cancer chemopreventive activity. See, Jang et al., *Science*, 275(5297), 218-220 (1997), Rimando et al., *J. Agric. Food Chem.*, 50(12), 3453-3457 (2002), Aggarwal et al., *Biochem. Pharmacol.*, 71(10), 1397-1421 (2006) and Baur et al., *Nat. Rev. Drug Discov.*, 5(6), 493-506 (2006). Stilbenes have been found in some berries (e.g., blueberries, cranberries, sparkleberries, lingonberries, grapes). See, Rimando et al., *J. Agric. Food Chem.*, 50(15), 4713-4719 (2004). Thus consumption of these small fruits may help improve health. Dietary black raspberries significantly suppressed the N-nitrosomethylbenzylamine (NMBA)-induced rat esophageal carcinogenesis. Chen et al., *Cancer Res.*, 66(5), 2853-2859 (2006).

The discovery of resveratrol as a cancer preventive agent has fostered interest in testing for the cancer preventive activity of other naturally occurring stilbenes in many laboratories. Notably pterostilbene, a dimethylether analog of resveratrol, was found to be as effective as resveratrol in preventing carcinogen-induced preneoplastic lesions in a mouse mammary organ culture (MMOC) model. Rimando et al., *J. Agric. Food Chem.*, 50(12), 3453-3457 (2002). Additionally, intravenous administration of pterostilbene to mice inhibited metastatic growth of B16M-F10 melanoma cells in the liver, a common site for metastasis development. Ferrer et al., *Neoplasia*, 7(1), 37-47 (2005).

Pterostilbene and resveratrol have very similar pharmacological properties. See, Rimando et al., *J. Agric. Food Chem.*, 50(12), 3453-3457 (2002) and Stivala et al., *J. Biol. Chem.*, 276(25), 22586-22594 (2001). In addition to the aforementioned activity in an MMOC model, both compounds are strong antioxidants and also hypolipidemic. See, Rimando et al., *J. Agric. Food Chem.*, 50(12), 3453-3457 (2002), Stivala et al., *J. Biol. Chem.*, 276(25), 22586-22594 (2001), Rimando et al., *J. Agric. Food Chem.*, 53(9), 3403-3407 (2005) and Miura et al., *Life Sci.*, 73(11), 1393-1400 (2003).

Pterostilbene is used as a chemical marker for extracts of *Pterocarpus marsupium*, from which it has been previously isolated and shown to lower serum glucose in rats. Manickam et al., *J. Nat. Prod.*, 60(6), 609-610 (1997). Resveratrol has been reported to reduce the growth of colorectal aberrant crypt foci (ACF) in rats. See, Tessitore et al., *Carcinogenesis*, 21(8), 1619-1622 (2000) and Sengottuvelan et al., *Carcinogenesis*, 27(5), 1308-1346 (2006). However, additional studies concerning the colon cancer preventive and treatment activities of stilbene compounds are needed.

SUMMARY OF INVENTION

The instant invention addresses these and other needs of the prior art. It has now been discovered that pterostilbene and analogs thereof possess anti-proliferative and anti-inflammatory action in colon cancer cells. Therefore, according to one aspect of the invention, an oral composition is provided for the prevention of colon cancer and colon inflammation containing a pharmaceutically acceptable carrier and an active compound of formula I:

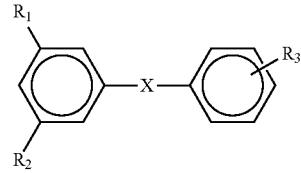

Formula I wherein X is selected from cis and trans alkynyl and cis and trans, substituted and unsubstituted, alkenyl;

$R_1$ and $R_2$ are independently selected from hydrogen, substituted and unsubstituted $C_1$-$C_3$ alkyls and $OR_4$, wherein $R_4$ is selected from hydrogen and substituted and unsubstituted $C_1$-$C_3$ alkyls;

$R_3$ is selected from hydrogen, halogens, glycosides, substituted and unsubstituted $C_1$-$C_3$ alkyls, $NO_2$, $H_2PO_4$, $SO_2R_4$, $OR_4$, $SR_4$, $COOR_4$, $COR_4$, $NR_5R_6$ and $COR_7$, wherein $R_4$, $R_5$, and $R_6$ are independently selected from hydrogen and substituted and unsubstituted $C_1$-$C_3$ alkyls; and $R_7$ is $NR_8R_9$, wherein $R_8$ and $R_9$ are independently selected from hydrogen and substituted and unsubstituted $C_1$-$C_3$ alkyls;

with a proviso that X, $R_1$, $R_2$ and $R_3$ may not be selected so that formula I is reservatrol.

According to one set of embodiments, the oral cancer-preventing compositions of the instant invention are nutraceutical compositions, which may be extracted from a plant product. In an additional set of embodiments, the oral cancer-preventing compositions may be incorporated within a protective coating, whereby the active ingredient is not substantially absorbed upstream of the small intestine of the subject and a quantity effective to prevent colon cancer is delivered to the large intestine.

The composition can also be used for treating colon inflammation. The present invention, therefore, also provides methods for treating colon inflammation with the oral composition of the present invention.

In another aspect, the invention provides a method of preventing colon cancer and colon inflammation in a subject by administering to the subject an effective amount of the oral compositions according to the previous aspects of the instant invention, and preferably the nutraceutical compositions of the present invention.

In another aspect, the instant invention provides compounds for the treatment of a colon cancer having a structure according to Formula I:

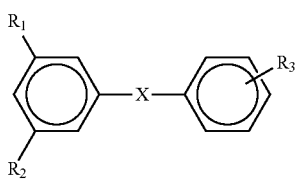

Formula I wherein X is selected from cis and trans alkynyl and cis and trans, substituted and unsubstituted alkenyl;

$R_1$ and $R_2$ are independently selected from hydrogen, substituted and unsubstituted $C_1$-$C_3$ alkyls and $OR_4$, wherein $R_4$ is selected from hydrogen and substituted and unsubstituted $C_1$-$C_3$ alkyls;

$R_3$ is selected from hydrogen, halogens, glycosides, substituted and unsubstituted $C_1$-$C_3$ alkyls, $NO_2$, $H_2PO_4$, $SO_4R_4$, $OR_4$, $SR_4$, $COOR_4$, $COR_4$, $NR_5R_6$ and $COR_7$, wherein $R_4$, $R_5$, and $R_6$ are independently selected from hydrogen and substituted and unsubstituted $C_1$-$C_3$ alkyls; and $R_7$ is $NR_8R_9$, wherein $R_8$ and $R_9$ are independently selected from hydrogen and substituted and unsubstituted $C_1$-$C_3$ alkyls;

with a proviso that X, $R_1$, $R_2$ and $R_3$ may not be selected so that formula I is reservatrol or pterostilbene.

In another aspect, the invention provides a method of treating colon cancer and colon inflammation in a subject in need thereof by administering to the subject an effective amount of the compound for the treatment of colon cancer according to the previous aspects of the instant invention.

The same compounds can also be used to prevent colon cancer and colon inflammation. Accordingly, the present invention also provides methods for preventing colon cancer and colon inflammation in a subject by administering to the subject the compounds of Formula I.

In addition, methods for treating or preventing colon cancer and colon inflammation are provided using pterostilbene and reservatrol. The methods administer to a subject in need thereof an effective amount of pterostilbene or reservatrol.

BRIEF DESCRIPTION OF THE DRAWINGS

FIG. 5 provides abbreviations used by the inventors to designate the stilbenes of FIG. 4.

DETAILED DESCRIPTION

Figure 1:
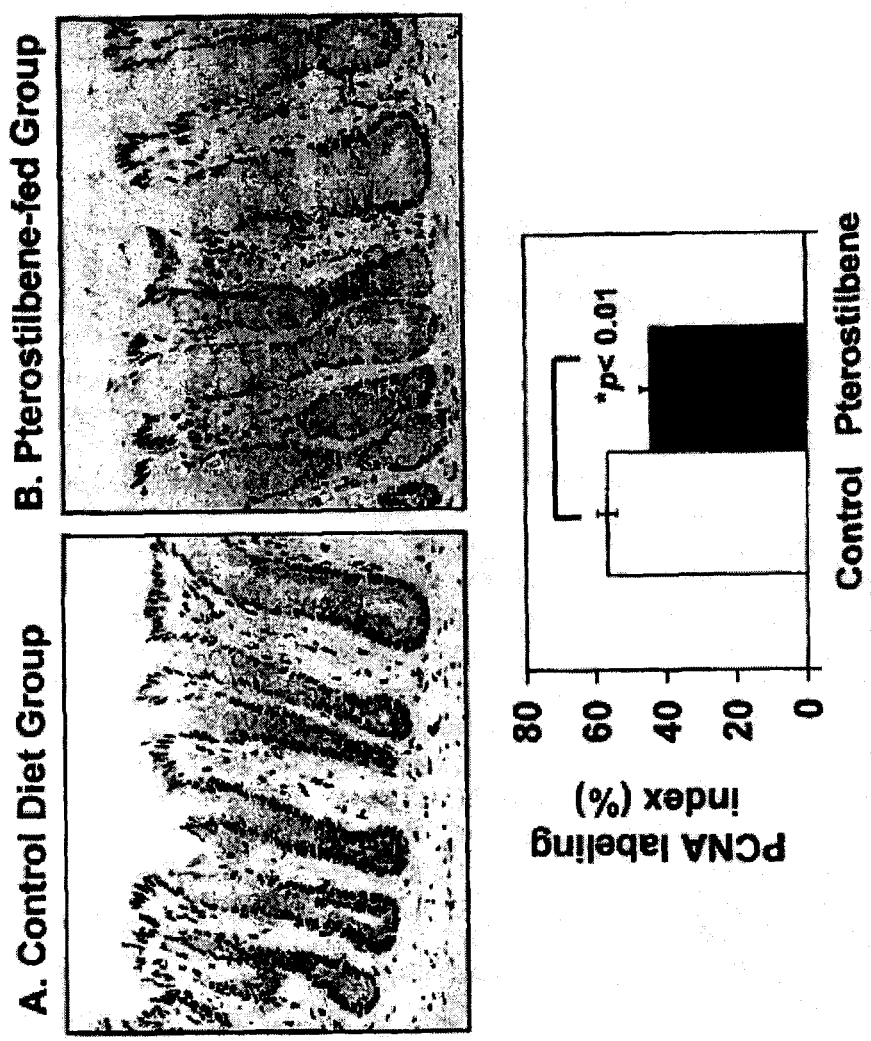
FIG. 1 illustrates PCNA labeling in colons of rats fed with control diet (A) and pterostilbene-containing diet (B).

For better understanding of the instant invention, the following non-limiting definitions have been used:

The phrase "not substantially absorbed into the gastrointestinal tract of the subject upstream of small intestine" refers to a lack of therapeutic effect due to absorption of the active ingredient which occurs before the composition enters small intestine (e.g., in the mouth, pharynx, esophagus, and stomach) of the subject.

The term "treating" or "treatment" of a disease refers to executing a protocol, which may include administering one or more drugs to a patient (human or otherwise), in an effort to alleviate signs or symptoms of the disease. The term "treating" or "treatment" does not require complete alleviation of signs or symptoms, does not require a cure, and specifically includes protocols which have only a marginal effect on the patient.

The inventors have surprisingly discovered that pterostilbene and pterostilbene analogs are efficient inhibitors of the formation of certain abnormalities which may be indicative of colon cancer.

Accordingly, in one aspect, the invention provides compounds for the prevention and treatment of colon cancer and colon inflammation in a subject. The compounds have a structure according to Formula I:

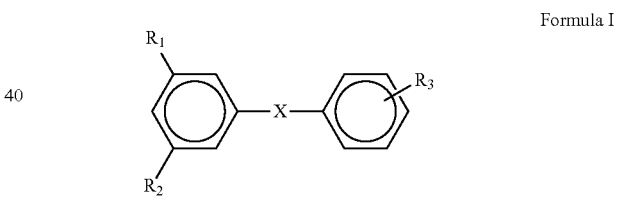

Formula I wherein X is selected from cis and trans alkynyl and cis and trans, substituted and unsubstituted, alkenyl;

$R_1$ and $R_2$ are independently selected from hydrogen, substituted and unsubstituted $C_1$-$C_3$ alkyls and $OR_4$, wherein $R_4$ is selected from hydrogen and substituted and unsubstituted $C_1$-$C_3$ alkyls;

$R_3$ is selected from hydrogen, halogens, glycosides, substituted and unsubstituted $C_1$-$C_3$ alkyls, $NO_2$, $H_2PO_4$, $SO_4R_4$, $OR_4$, $SR_4$, $COOR_4$, $COR_4$, $NR_5R_6$ and $COR_7$, wherein $R_4$, $R_5$, and $R_6$ are independently selected from hydrogen and substituted and unsubstituted $C_1$-$C_3$ alkyls; and $R_7$ is $NR_8R_9$, wherein $R_8$ and $R_9$ are independently selected from hydrogen and substituted and unsubstituted $C_1$-$C_3$ alkyls.

X, $R_1$, $R_2$ and $R_3$ may not be selected so that formula I is a known compound such as reservatrol or pterostilbene. However, known compounds may be used for treatment and preventative methods in which their use for such purpose was heretofore unknown.

X is preferably an two or three carbon alkenyl. When substituted, X is preferably methyl-substituted. The $C_1$-$C_3$ substituted alkyls of $R_1$, $R_2$, $R_3$, $R_4$, $R_5$, $R_6$, $R_8$ and $R_9$ are preferably substituted with OH, methyl or one to three halogens. Preferred halogens for $R_1$, $R_2$ and the $C_1$-$C_3$ substituted alkyls are F, Cl and Br. The preferred glycoside is glucose, and more preferably α-D-glucose.

In a preferred set of embodiments, the compounds may be described by Formula II, III or IV as follows:

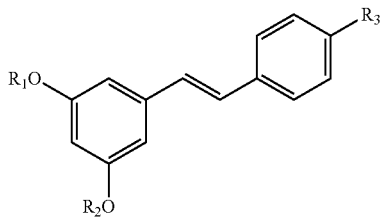

Formula II wherein $R_1$ and $R_2$ are independently selected from hydrogen and substituted and unsubstituted $C_1$-$C_3$ alkyls;

$R_3$ is selected from hydrogen, hydroxy, fluorine, chlorine, bromine, glucose, substituted and unsubstituted $C_1$-$C_3$ alkyls, $H_2PO_4$, $NO_2$, $NH_2$, SH and $COOR_4$, wherein $R_4$ is selected from hydrogen, and substituted and unsubstituted $C_1$-$C_3$ alkyls.

In one preferred set of embodiments, $R_1=R_2=CH_3$ and $R_3$ is selected from $OR_4$, $SR_4$, fluorine, chlorine, bromine, glucose, $NO_2$, $COOR_4$ and $NR_4R_5$, wherein $R_4$ and $R_5$ are independently selected from H and $CH_3$.

Formula III is as follows:

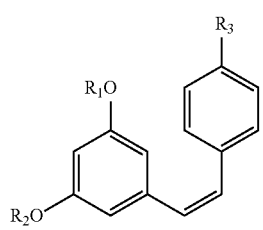

Formula III wherein $R_1$ and $R_2$ are independently selected from hydrogen and substituted and unsubstituted $C_1$-$C_3$ alkyls; and $R_3$ is selected from hydrogen, hydroxy, fluorine, chlorine, bromine, glucose, substituted and unsubstituted $C_1$-$C_3$ alkyls, $NO_2$, $OR_4$, $SR_4$, $COOR_4$ and $NR_5R_6$ wherein $R_4$ is selected from substituted and unsubstituted $C_1$-$C_3$ alkyls and $R_5$ and $R_6$ are independently selected from hydrogen and substituted and unsubstituted $C_1$-$C_3$ alkyls.

In one preferred set of embodiments, $R_1=R_2=CH_3$ and $R_3$ is selected from $OCH_3$, $NO_2$, $COOR_4$ and $NR_5R_6$, wherein $R_4$ is $CH_3$ or $C_2H_5$, and $R_5$ and $R_6$ are independently selected from H and $CH_3$.

In one embodiment of the invention, the compound is pterostilbene, i.e., the compound of formula IV.

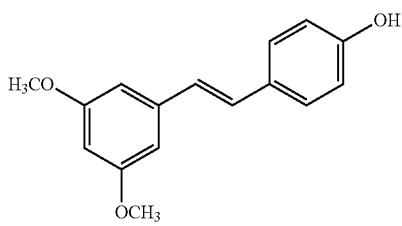

Formula IV

Preferred compounds include pterostilbene, (E)-1,3-dimethoxy-5-(4-nitrostyryl)benzene, (Z)-1,3-dimethoxy-5-(4-nitrostyryl)benzene, (E)-4-(3,5-dimethoxystyryl)aniline, (Z)-4-(3,5-di-methoxystyryl) aniline, (E)-methyl-4-(3,5-dimethoxystyryl)benzoate, (Z)-methyl-4-(3,5-dimethoxystyryl)benzoate, (E)-4-3,5-dimethoxystyryl)benzoic acid, (Z)-4-(3,5-dimethoxy-styryl)benzoic acid, (E)-1,3-dimethoxy-5-(4-methoxystyryl)benzene, (Z)-1,3-dimethoxy-5-(4-methoxystyryl)benzene, (E)-3-(4-hydroxystyryl)-5-methoxyphenol, 4-(3,5-dimethoxyphen-ethyl)phenol, (E)-5-(4-methoxystyryl)benzene-1,3-diol, (Z)-5-(4-methoxystyryl)benzene-1,3-diol and (E)-4-(3,5-dimethoxystyryl)phenyl dihydrogen phosphate.

More preferred compounds include pterostilbene, (E)-1,3-dimeth-oxy-5-(4-nitrostyryl)benzene, (Z)-1,3-dimethoxy-5-(4-nitrostyryl)benzene, (E)-4-(3,5-dimethoxystyryl) aniline, (Z)-4-(3,5-di-methoxystyryl) aniline, (Z)-methyl-4-(3,5-dimethoxy-styryl)benzoate, (E)-1,3-dimethoxy-5-(4-methoxystyryl)benzene and (Z)-1,3-dimethoxy-5-(4-methoxystyryl)benzene.

Particularly preferred compounds include pterostilbene, (E)-4-(3,5-dimethoxystyryl) aniline, (Z)-methyl-4-(3,5-dimethoxystyryl)benzoate and (Z)-1,3-dimethoxy-5-(4-methoxystyryl)benzene.

Figure 13:
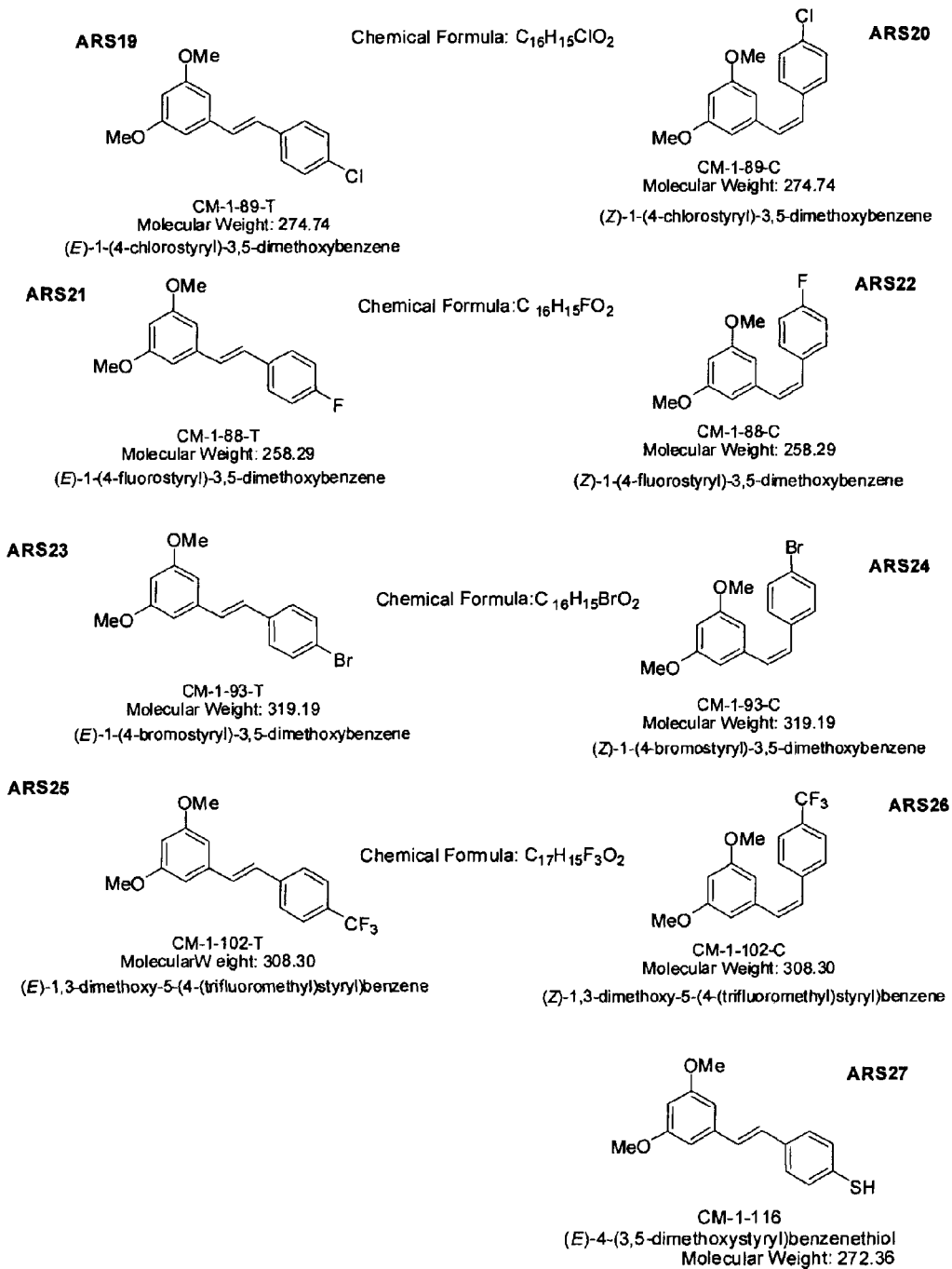
FIG. 13 is an illustration of formulae of other selected stilbenes used for some experiments of the instant invention.

The compounds of the instant invention may be prepared by a variety of routine methods. For the names and structures of compounds ARS1-ARS17 and ARS19-ARS27, see FIGS. 4-5 and FIG. 13, respectively. For example, these compounds may be chemically synthesized by the procedures employed in the Examples. Compounds ARS1, ARS2, ARS5, ARS6, ARS9, ARS12, ARS13 and ARS19-ARS26 were synthesized through the Wittig reaction where phosphonium salts were reacted with suitable aromatic aldehydes.

The synthesis of ARS3 and ARS4 were achieved by the reduction of nitro derivative ARS1 and ARS2 using sodium dithionite. ARS7 and ARS17 were synthesized by the reduction of esters ARS5 and ARS6 using NaOH in methanol. Methylation of pterostilbene using $K_2CO_3$ and iodomethane afforded ARS8. Demethylation of pterostilbene using lithium thioethoxide in DMF gave ARS10. Reduction of the vinyl double bond using Pd/C gave ARS11.

Synthesis of ARS14 was achieved by reaction of pterostilbene with dibenzyl phosphate followed by deprotection of the benzyl group with bromotrimethylsilane. Synthesis of the thiol derivative ARS27 was accomplished by reaction of pterostilbene with dimethyl thiocarbamoyl chloride using triethylamine and DMAP in dioxane, followed by rearrangement using KOH.

In other embodiments, the naturally occurring active ingredients, e.g., pterostilbene, may be extracted from a plant product by conventional means. As discussed above, it has been found the pterostilbene is present in multiple plants (e.g., red sandalwood (*Pterocarpus santalinus*)) and plant products, including fruits or berries such as, for example, grapes, blueberries and the like.

The compounds of the present invention may be formulated as oral compositions for the prevention of colon cancer or for the prevention and treatment of colon inflammation. The oral compositions according to the present invention do not include compositions comprising substantial amounts of reservatrol. The dosage forms of the oral composition of the present invention may comprise auxiliary, excipients such as, for example, lubricants, plasticizers, anti-tack agents, opacifying agents, pigments, and the like. As will be appreciated by those skilled in the art, the exact choice of excipient and their relative amounts will depend to some extent on the final oral dosage form. The composition may be formulated as a tablet, a granule, a capsule, a gel, a confectionary, a caplet, a syrup, and the like.

In another advantageous embodiment of the invention, the composition is formulated to delay the release of the active ingredient until the composition reaches the small intestine, and, preferably, the large intestine of the subject. This objective may be achieved by formulating the active ingredient with one or more protective compounds, typically in a coating on the oral dosage form.

It is known that different part of the gastrointestinal tract have widely different pH. For example, the pH of the stomach content is about 1 and may get as low as 1. In contrast, the pH of the proximal parts of the small intestine ranges between about 4.7 and about 6.5. The pH gradually increases in distal parts of the small intestine and reaches about 7.5-8.0 in the large intestine. Accordingly, by controlling the thickness and the pH of the enteric coating it is be possible to deliver the active ingredient to the large intestine without chemical damage and without the loss of the active ingredient caused by its absorption in upper parts of the gastrointestinal tract. Essentially, the protective compound would have a pH greater than about 4, and preferably, pH approaching that of the large intestine of the subject.

Examples of suitable gastro-resistant substances include, but are not limited to, alginic acid, acrylic and methacrylic acid polymers and copolymers or cellulose derivatives, glyceryl monostearate, glyceryl palmitostearate, carnauba wax, microcrystalline wax, white wax, yellow wax, and ethylcellulose with less than 47% of ethonyl groups, as described in Handbook of Pharmaceutical Excipients, Fourth Edition, (edited by Rowe, Sheckey, and Weller, Pharmaceutical Press, 2003). Formulations according to embodiments of the present invention may comprise auxiliary excipients such as for example diluents, binders, lubricants, surfactants, disintegrants, plasticizers, anti-tack agents, opacifying agents, pigments, and the like. The exact choice of excipient and relative amounts depend to some extent on the final oral dosage form.

Suitable diluents include, for example, pharmaceutically acceptable inert fillers such as microcrystalline cellulose, lactose, starch, dibasic calcium phosphate, saccharides, and/or mixtures of the foregoing. Examples of microcrystalline celluloses include (Avicel PH 200, Avicel PH 102, Avicel PH 112, Avicel PH 101, Avicel PH 3020. Non-limiting examples of lactose include lactose monohydrate. In addition, mannitol, sucrose, and dextrose may be used.

Suitable binders include, for example, starch, povidone, low viscosity hydroxypropylmethylcellulose such as Methocel E-5 Prem. LV, pregelatinised starch, hydroxypropyl-cellulose and/or mixtures of the foregoing. Suitable disintegrants include, for example, crosslinked polyvinyl pyrrolidone, various starches, such as potato starch, corn starch, rice starch, and modified starches, crospovidone, sodium starch glycollate croscarmellose sodium, and the like or mixtures thereof. Suitable lubricants, including agents that act on the flowability of the powder to be compressed are, for example, colloidal silicon dioxide such as Aerosil® 200; talc; stearic acid, magnesium stearate, calcium stearate and sodium stearyl fumarate. The formulation of the gastro-resistant coating on oral dosage forms using such substances is essentially conventional and well understood by those of ordinary skill in the art.

The oral composition according to embodiments of the present invention may be prepared by many methods known to a skilled artisan. For example, granules for preparing tablets according to the invention can be manufactured in accordance with standard procedures in which the active ingredient may be combined with suitable excipients prior to mixing and forming compressible granules by adding solution of a binder in a low or high shear mixer or by fluidized bed granulation. The granules are dried, preferably in a fluidized bed dryer. The dried granules are sieved and mixed with lubricants and disintegrants. Alternatively, the manufacture of granules can be achieved by direct mixing of the directly compressible excipients or by roller compaction.

In another embodiment, the present invention comprises a composition including the active ingredient and one or more protective compounds, serving as coating agents for the formulation. Non-limiting examples of protective compounds suitable for coating are carnauba wax, micro-crystalline wax, white wax, yellow wax, and ethyl cellulose with less than 46.5% of ethonyl groups. It is preferred that amount of gastro-resistant coating applied is from 5% to 30% by weight with regard to the total weight of the composition.

The first step of the process for the preparation of the composition with controlled release of the active ingredient is anhydrous granulation of the active ingredient (whether in the pure form or as a part of the dried extract of a plant product) and dried pharmaceutically acceptable auxiliary substances so that their weight loss at drying is preferably less than 1.0%. Organic solvents to be used in the process of anhydrous granulation should, preferably, contain less than 0.2% of water. The process of anhydrous granulation is carried out in such a way that a dried surfactant is dissolved in an organic solvent at room temperature and the obtained solution is sprayed in a fluidized bed granulator onto a homogenous powdery mixture containing the active ingredient, a dried binder soluble in organic solvents, a dried cellulose ether and other dried pharmaceutically acceptable auxiliary substances.

The organic solvents to be used for that purpose are selected from the group of alcohols, ketones, esters, ethers, aliphatic hydrocarbons, halogenated hydro-carbons, cycloaliphatic, aromatic, heterocyclic solvents and mixtures thereof. The plastic mixture obtained in the process of anhydrous granulation is formed into granules or pellet cores by common pharmaceutical technological processes such as extruding and spheronizing methods. The pellet cores or granules so formed are dried in a fluidized bed or in a chamber dryer at the temperature of inlet air from 35° C. to 45° C. until the weight loss at drying is less than 1.0% of the total weight of the pellet cores or granules.

Under the addition of dried pharmaceutically acceptable auxiliary substances, dry pellet cores or granules may be compressed into tablets, which in further procedure are coated with the selected coating. In view of the porosity of the tablets, also one or more intermediate coatings may be applied between the tablet and the coating. Alternatively, pellet cores or granules prepared by means of anhydrous granulation may be coated with the protective compound coating and then filled into capsules or bags or compressed into tablets under addition of dried pharmaceutically acceptable auxiliary substances. In view of the porosity of pellet cores or granules, also one or more intermediate coatings may be applied between the pellet core or granule and the protective coating.

In another aspect, the invention provides a method of cancer prevention comprising administering to a subject in need thereof an oral composition of any embodiment described above. In one embodiment, the subject is at risk of colon cancer. The risk factors of colon cancer have been known in the art and described, for example, on the web site of American Cancer Society (http://www.cancer.org/docroot/CRI/content/CRI_2_4_2X_What_are_the_risk_factors-_for_colon_and_rectum_cancer.asp, last accessed on Dec. 3, 2007). Risk factors include, without limitation, age, high fat diet, incidence of colon cancer in the family, personal history of colorectal polyps, personal history of colorectal cancer, a personal history of inflammatory bowel disease, smoking, diabetes, low exercise, racial (African-Americans) or ethnic (Ashkenazi Jews) background, obesity, alcohol intake, exposure to carcinogens, such as, for example, azoxymethane.

As disclosed above, the Formula I compounds of the instant invention may be used to treat colon cancer and treat or prevent colon inflammation. In one embodiment the selected compound or compounds are formulated into a pharmaceutical composition.

In practice, a composition for treating colon cancer or for treating or preventing inflammation containing a compound of formulas I-IV may be administered in any variety of suitable forms, for example, topically, parenterally, rectally, or orally. More specific routes of administration include intravenous, intramuscular, subcutaneous, colonical, peritoneal, transepithelial including transdermal, sublingual, buccal, dermal and the like.

A composition containing a compound of formulas I-IV may be presented in forms permitting administration by the most suitable route. The invention also relates to administering compositions containing a compound of formulas I-IV which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formulas I-IV in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formulas I-IV may be incorporated into sustained-release preparations and formulations.

For oral administration, the composition may further comprise any of the protective compounds described above, including, without limitation gastro-resistant compounds and enteric coatings.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants.

Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formulas I-IV as a free base or pharmacologically acceptable salt can be prepared in water suitably mixed with a surfactant such as hydroxypropyl-cellulose.

Dispersions can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, or by various antibacterial and antifungal agents, for example, parabens, chlorobutanol, phenol, sorbic acid, thimerosal, and the like.

Sterile injectable solutions are prepared by incorporating the compound of formulas I-IV in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of formulas I-IV may be used. The compound of formulas I-IV may be also incorporated in a gel or matrix base for application in a patch, which would allow a controlled release of compound through transdermal barrier.

The percentage of compound of formulas I-IV in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient.

In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of formulas I-IV used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of formulas I-IV may be administered 1 to 4 times per day. Of course, for other patients, it will be necessary to prescribe not more than one or two doses per day. Treatment or preventative methods according to the present invention may also use pterostilbene and reservatrol.

Specific embodiments according to the methods of the present invention will now be described in the following non-limiting examples.

EXAMPLES

Examples 1-7

General Procedure for Stilbenes Synthesis (ARS1, ARS2, ARS5, ARS6, ARS9, ARS23 and ARS24)

To a cold solution (−78° C.) of phosphonium salt (1.0 equiv) in THF was added n-butyllithium (1.6M in hexanes, 1.0 equiv) and the resulting solution stirred under inert atmosphere for 2 h. A solution of aldehyde (1.0 equiv) in THF was added dropwise, and the mixture was stirred for 12 h at room temperature. The resulting suspension was poured into water and extracted with dichloromethane. The organic phase was dried over $MgSO_4$ and concentrated under reduced pressure. The crude product was purified through automated flash purification eluting with hexanes/ethyl acetate (97:3). The cis isomer was eluted first followed by the trans isomer.

ARS1: (E)-1,3-dimethoxy-5-(4-nitrostyryl)benzene. Yellow solid. $^1$H NMR ($CDCl_3$, 400 MHz): δ 3.83 (s, 6H); 6.45 (s, 1H); 6.68 (s, 2H); 7.07-7.16 (m, 1H); 7.23 (d, 1H, J=36); 7.61 (d, 2H, J=8); 8.20 (d, 2H, J=8). $^{13}$C NMR ($CDCl_3$, 400 MHz): δ 55.4 (2 C), 100.9, 105.0 (2 C), 124.1 (2 C), 126.7, 126.9 (2 C), 133.2, 138.1, 143.6, 146.7, 161.0 (2 C). HRMS: Calc for $C_{32}H_{30}N_2O_8Na$ 593.18998. Found 593.18332 (2M+Na).

ARS2: (Z)-1,3-dimethoxy-5-(4-nitrostyryl)benzene. $^1$H NMR ($CDCl_3$, 400 MHz): δ 3.66 (s, 6H); 6.34-6.35 (m, 3H); 6.58 (d, 1H, J=12); 6.74 (d, 1H, J=16); 7.39 (d, 2H, J=8); 8.07 (d, 2H, J=8). $^{13}$C NMR ($CDCl_3$, 400 MHz): δ 55.4 (2 C), 100.3, 106.9 (2 C), 123.6 (2 C), 128.5, 129.9 (2 C), 134.1, 138.2, 144.2, 146.7, 161.0 (2 C). HRMS: Calc for $C_{32}H_{30}N_2O_8$ Na 593.18998. Found 593.18987 (2M+Na).

ARS5: (E)-Methyl 4-(3,5-dimethoxystyryl)benzoate. White solid. $^1$H NMR ($CDCl_3$, 400 MHz): δ 3.83 (s, 6H); 3.92 (s, 3H); 6.42 (s, 1H); 6.68 (s, 2H); 7.07-7.16 (m, 2H); 7.55 (d, 2H, J=8); 8.02 (d, 2H, J=8). $^{13}$C NMR ($CDCl_3$, 400 MHz): δ 52.3, 55.5 (2 C), 100.7, 105.0 (2 C), 126.6 (2 C), 128.2, 129.1, 130.2 (2 C), 131.4, 138.9, 141.8, 161.2 (2 C), 167. HRMS: Calc for $C_{36}H_{36}NaO_8$ 619.23079. Found 619.22594 (2M+Na).

ARS6: (Z)-Methyl 4-(3,5-dimethoxystyryl)benzoate. Viscous liquid. $^1$H NMR ($CDCl_3$, 400 MHz): δ 3.63 (s, 6H), 3.88 (s, 3H), 6.33 9 s, 1H), 6.36 (s, 2H), 6.57 (dd, 2H, $J_{1,2}$=12, $J_{1,3}$=8), 7.32 (d, 2H, J=8), 7.90 (d, 2H, J=8). $^{13}$C NMR ($CDCl_3$, 400 MHz): δ 52.0, 55.1 (2 C), 100.0, 106.7 (2 C), 128.6, 128.9 (2 C), 129.4 (2 C), 129.5, 132.1, 138.4, 142.0, 160.6 (2 C), 166.8. HRMS: Calc for $C_{36}H_{36}NaO_8$ 619.23079. Found 619.22729 (2M+Na).

ARS9: (Z)-1,3-dimethoxy-5-(4-methoxystyryl)benzene. Viscous liquid. $^1$H NMR ($CDCl_3$, 400 MHz): δ 3.69 (s, 6H); 3.78 (s, 3H); 6.37 (s, 1H); 6.46-6.49 (m, 3H); 6.55 (d, 1H, J=12); 6.80 (d, 2H, J=8); 7.26 (d, 2H, J=8). $^{13}$C NMR ($CDCl_3$, 400 MHz): δ 55.4 (2 C), 99.6, 106.6 (2 C), 113.2 (2 C), 128.7, 129.5, 130.2 (2 C), 130.3 (2 C), 139.5, 158.8, 160.6 (2 C). HRMS: Calc for $C_{34}H_{36}NaO_6$ 563.24096. Found 563.24396 (2M+Na).

Physical data, including mass spectra and IR spectra measurements were also obtained for ARS23 and ARS24.

Examples 8-11

General Procedure for Synthesis of ARS19, ARS20, ARS25 and ARS26

To a solution of (3,5-dimethoxybenzyl)triphenylphosphonium bromide (300 mg, 0.6 mM) in DCM was added benzaldehyde (85 mg, 0.6 mM), 18-crown-6 (16 mg, 0.06 mM) and potassium hydroxide (102 mg, 1.8 mM). The mixture was stirred at room temperature for 12 h. DCM was added and the organic phase was washed with water. The organic phase was dried over $MgSO_4$ and concentrated under reduced pressure. The crude product was purified through automated flash purification eluting with hexanes/ethyl acetate (89:11).

Physical data, including mass spectra and IR spectra measurements were obtained for ARS19, ARS20, ARS25 and ARS26.

Examples 12 and 13

General Procedure for Synthesis of (Z) and (E) 1-(4-fluorostyryl)-3,5-dimethoxybenzene ARS21 and ARS22

To a solution of (3,5-dimethoxybenzyl)triphenylphosphonium bromide (300 mg, 0.6 mM), 4-fluorobenzaldehyde (133 mg, 1.07 mM), catalytic amounts of 18 crown-6 in DCM was added 1.5 mL of 50% solution of NaOH. The reaction was stirred for 5 h and water was added. The water phase was extracted with ethyl acetate and the organic phase was combined. The crude product was purified through flash chromatography eluting with hexanes/ethyl acetate (98:2).

Physical data, including mass spectra and IR spectra measurements were obtained for ARS21 and ARS22.

Examples 14 and 15

(Z) and (E)-5-(4-methoxystyryl)benzene-1,3-diol ARS12 and ARS13

Reaction of 3,5-bis(tert-butyldimethylsilyloxy)benzaldehyde (408 mg, 1.11 mM) and (4-methoxybenzyl)triphenylphosphonium bromide (500 mg, 1.11 mM) afforded 452 mg (86% yield) of mixture of cis and trans stilbenes. Due to difficulties found in separating the two isomers, deprotection of TBS group was followed without isolation of the isomers. Tetrabutylammonium fluoride (2.5 mL, 2.5 mM) was added to a mixture of (E) and (Z)-(5-(4-methoxystyryl)-1,3-phenylene) bis(oxy)bis(tert-butyldimethylsilane) (452 mg, 0.96 mM) in anhydrous tetrahydrofuran (10 mL). The solution was stirred for 45 min, poured into water and extracted with ether. After removal of the solid, the resulting crude mixture was purified using flash chromatography (7:3 hexanes/ethyl acetate).

ARS12: (E)-5-(4-methoxystyryl)benzene-1,3-diol. $^1$H NMR (MeOD, 400 MHz): δ4.87 (s, 3H); 6.17 (s, 1H), 6.46 (s, 2H); 6.82 (d, 1H, J=16); 6.87 (d, 2H, J=8); 6.97 (d, 1H, J=16); 7.41 (d, 2H, J=8). $^{13}$C NMR (MeOD, 400 MHz): δ 58.5, 105.6, 108.7 (2 C), 117.9 (2 C), 130.5, 131.5 (2 C), 131.9, 134.2, 144, 162.4 (2 C), 163.5. HRMS: Calc for $C_{15}H_{13}O_3$ 241.08647. Found 241.08863 (M−H).

ARS13: (Z)-5-(4-methoxystyryl)benzene-1,3-diol. $^1$HNMR (MeOD, 400 MHz): δ 3.70 (s, 3H); 6.18 (s, 1H); 6.32 (s, 2H), 6.33 (d, 1H, J=12); 6.47 (d, 1H, J=12); 6.73 (d, 2H, J=8); 7.18 (d, 2H, J=8). $^{13}$C NMR (DMSO, 400 MHz): δ 58.4, 105.2, 111.1, 117.3 (2 C), 132.5, 133.5, 133.7 (2 C), 134.1 (2 C), 143.9, 162 (2 C), 162.9. HRMS: Calc for $C_{15}H_{13}O_3$ 241.08647. Found 241.08735 (M−H).

Examples 16 and 17

General Procedure for Synthesis of (E) and (Z)-4-(3,5-dimethoxystyryl)aniline ARS3 and ARS4

A solution of trans nitro derivative ARS1 (45 mg, 0.15 mM) in acetone/water (10:5 mL) was heated to 50° C. for 30 min. Sodium dithionite (686 mg, 3.75 mM) was slowly added and the mixture was heated to reflux for 1 h. After cooled to room temperature the mixture was poured into water and extracted with ethyl acetate. The organic phase was dried over MgSO$_4$ and solvent was removed under reduced pressure. The crude mixture was purified using automated flash chromatography eluting with hexanes:ethyl acetate (75:25) and gave ARS3.

ARS3: (E)-4-(3,5-dimethoxystyryl)aniline. Yellow solid. $^1$H NMR (CDCl$_3$, 400 MHz): δ 3.82 (s, 6H); 6.37 (s, 1H); 6.65-6.68 (m, 4H); 6.86 (d, 1H, J=16); 7.01 (d, 1H, J=16); 7.33 (d, 2H, J=8). $^{13}$C NMR (CDCl$_3$, 400 MHz): δ 55.5 (2 C), 99.6, 104.4 (2 C), 115.5 (2 C), 125.2, 128, 128.1 (2 C), 129.5, 140.2, 146.4, 161.2 (2 C). HRMS: Calc for $C_{16}H_{18}NO_2$ 256.13375. Found 256.14321 (M+H).

ARS4: (Z)-4-(3,5-dimethoxystyryl)aniline. Yellow solid. $^1$H NMR (CDCl$_3$, 400 MHz): δ 3.68 (s, 6H); 6.32 (s, 1H); 6.39 (s, 1H); 6.47 (m, 3H); 6.54 (d, 2H, J=8); 7.11 (d, 2H, J=8). $^{13}$C NMR (CDCl$_3$, 400 MHz): δ 55.4 (2 C), 99.7, 106.8 (2 C), 114.8 (2 C), 127.6, 127.7, 130.4 (2 C), 130.8, 140.1, 145.7, 160.7 (2 C). HRMS: Calc for $C_{16}H_{18}NO_2$ 256.13375. Found 256.10757 (M+H)

Examples 18 and 19

General Procedure for Synthesis of (Z) and (E)-4-(3,5-dimethoxystyryl)benzoic acid ARS7 and ARS17

To a solution of ARS5 (50 mg, 0.16 mM) in THF was added NaOH 1N solution (335 μL). The reaction was left stirring at reflux for 3 days and NaOH was added from time to time until starting material disappeared. The mixture was poured into water, the pH was brought to neutral and the mixture was extracted with ethyl acetate. The organic phase was dried over MgSO$_4$ and concentrated. The crude material was purified using automated flash chromatography eluting with chloroform:methanol (9:1).

ARS7: (E)-4-(3,5-dimethoxystyryl)benzoic acid. White solid. $^1$H NMR (DMSO, 400 MHz): δ 3.74 (s, 6H); 6.41 (s, 1H); 6.78 (s, 2H); 7.29 (d, 2H, J=4); 7.67 (d, 2H, J=8); 7.91 (d, 2H, J=8). $^{13}$C NMR (DMSO, 400 MHz): δ 55.9 (2 C), 101, 105.4 (2 C), 127.8 (2 C), 128.6, 130.2, 130.4 (2 C), 131.6, 139.3, 142, 161.3 (2 C), 167.8 HRMS: Calc for $C_{17}H_{15}O_4$ 283.09703. Found 283.09726 (M−H).

ARS17: (Z)-4-(3,5-dimethoxystyryl)benzoic acid. White solid. $^1$H NMR (DMSO, 400 MHz): δ 3.56 (s, 6H); 6.31-6.34 (m, 3H); 6.64 (s, 2H); 7.30 (d, 2H, J=8); 7.80 (d, 2H, J=8). $^{13}$C NMR (DMSO, 400 MHz): δ 55.4 (2 C), 100, 107 (2 C), 129.1 (2 C), 129.7 (3 C), 130.3, 132, 138.5, 141.7, 160.7 (2 C), 167.8. HRMS: Calc for $C_{17}H_{15}O_4$ 283.09703. Found 283.09681 (M−H).

Example 20

Synthesis of (E)-1,3-dimethoxy-5-(4-methoxystyryl)benzene ARS8

To a solution of pterostilbene (100 mg, 0.39 mM) in DMF was added potassium carbonate (108 mg, 0.78 mM). The reaction stirred for 30 min and methyl iodide was added (37 μL, 0.58 mM). The mixture was stirred for 12 h at room temperature and poured into water. The mixture was extracted with ethyl acetate and the crude purified using flash chromatography eluting with ethyl acetate/hexanes (4:1).

ARS8: (E)-1,3-dimethoxy-5-(4-methoxystyryl)benzene. White solid. $^1$H NMR (CDCl$_3$, 400 MHz): δ 3.83 (s, 9H); 6.39 (s, 1H); 6.67 (s, 2H); 6.89 (s, 2H); 6.92 (d, 1H, J=8); 7.02 (d, 1H, J=8); 7.45 (d, 2H, J=8). $^{13}$C NMR (CDCl$_3$, 400 MHz): δ 55.3 (3 C), 99.6, 104.3 (2 C), 114.1 (2 C), 126.5, 127.8 (2 C), 128.7, 129.9, 139.7, 159.4, 161.0 (2 C). HRMS: Calc for $C_{34}H_{36}NaO_6$ 563.24096. Found 563.24419 (2M+Na).

Example 21

4-(3,5-dimethoxyphenethyl)phenol ARS11

Pd/C (catalytic) was added to a solution of pterostilbene 2 (50 mg, 0.195 mM) in methanol. The mixture was left stirring overnight under H$_2$ at room temperature. The mixture was filtered and the solvent evaporated under reduced pressure. The crude mixture was purified using flash chromatography eluting with hexanes:ethyl acetate (7:3).

ARS11: 4-(3,5-dimethoxyphenethyl)phenol. $^1$H NMR (CDCl$_3$, 400 MHz): δ 2.84 (s, 4H), 3.78 (s, 6H), 6.34-6.35 (m, 4H); 6.76 (d, 2H, J=8); 7.05 (d, 2H, J=8). $^{13}$C NMR (CDCl$_3$, 400 MHz): δ 36.7, 38.4, 55.2 (2 C), 97.9, 106.6 (2 C), 115.1 (2 C), 129.5 (2 C), 133.8, 144.2, 153.7, 160.6 (2 C). HRMS: Calc for $C_{16}H_{17}O_3$ 257.11777. Found 257.11889 (M−H).

Example 22

(E)-4-(3,5-dimethoxystyryl)phenyl dihydrogen phosphate ARS14

To a cold mixture (−10° C.) of pterostilbene (200 mg, 0.67 mM) and N,N-(dimethylamino)pyridine (10.2 mg, 0.083 mM) in anhydrous acetonitrile (10 mL) was added carbon tetrachloride (323 μL, 3.35 mM) and DIEA (245 μL, 1.4 mM). The mixture was left stirring at −10° C. for 30 min and dibenzyl phosphate (224 μL, 1 mM) was added. The solution was stirred for 12 h at room temperature and poured into 0.5M monobasic potassium phosphate. The mixture was extracted with ethyl acetate and the organic phase dried over MgSO$_4$. The solvent was evaporated, the crude mixture was purified by column chromatography eluting with hexanes:ethyl acetate (7:3) and afforded (E)-dibenzyl 4-(3,5-dimethoxystyryl)phenyl phosphate.

Bromotrimethylsilane (80 μL, 0.61 mM) was added to a solution of (E)-dibenzyl 4-(3,5-dimethoxystyryl)phenyl phosphate (150 mg, 0.29 mM) in anhydrous dichloromethane (10 mL) at 0° C. After 2 h stirring at room temperature, water was added and the solution was stirred for 1 h. The mixture was extracted with ethyl acetate and the organic phase was dried over MgSO$_4$. The solvent was removed and afforded 38.6 (39% yield) of the desired compound.

ARS14: (E)-4-(3,5-dimethoxystyryl)phenyl dihydrogen phosphate. $^1$H NMR (CDCl$_3$, 400 MHz): δ 3.63 (s, 6H); 6.23 (s, 1H); 6.40 (s, 2H), 6.60 (d, 1H, J=16), 6.71 (d, 1H, J=16);

7.02-7.14 (m, 4H), 9.11 (bs, 2H). $^{13}$C NMR (CDCl$_3$, 400 MHz): δ 58.6 (2 C), 103.5, 108.2 (2 C), 124.4, 131.4 (3 C), 131.8, 132.1, 137.2, 143.6, 156, 165.1 (2 C). HRMS: Calc for C$_{16}$H$_{17}$O$_6$P 335.06845. Found 335.07300 (M–H).

Example 23

(E)-3-(4-hydroxystyryl)-5-methoxyphenol ARS10

To a solution of pterostilbene (30 mg, 0.11 mM) in DMF (10 mL) was added lithium thioethoxide. (135 mg). the solution was heated at 160° C. for 2 h. After cool, 15 mL of HCl 0.1M was added and the mixture was extracted with ethyl acetate. The solvent was removed under reduced pressure and the crude mixture was purified using flash chromatography eluting with hexanes:ethyl acetate (3:2).

ARS10: (E)-3-(4-hydroxystyryl)-5-methoxyphenol. $^1$H NMR (MeOD, 400 MHz): δ 4.88 (s, 3H); 6.24 (s, 1H); 6.54 (s, 2H); 6.76 (d, 2H, J=8); 6.83 (d, 1H, J=16); 6.99 (d, 1H, J=16); 7.35 (d, 2H, J=8). $^{13}$C NMR (MeOD, 400 MHz): δ 54.5, 100.2, 103.3, 105.5, 115.3 (2 C), 125.8, 127.7 (2 C), 128.5, 129.2, 140.2, 157.6, 158.4, 161.3. HRMS: Calc for C$_{15}$H$_{13}$O$_3$ 241.08647. Found 241.08672 (M–H).

Example 24

(E)-2-(4-(3,5-dimethoxystyryl)phenoxy)-6-(hydroxylmethyl)tetrahydro-2H-pyran-3,4,5-triol ARS18

To a solution of acetobromo-α-D-glucose (48 mg, 0.11 mM) and benzyltriethylammonium bromide (13 mg, 0.04 mM) in chloroform was added a solution of pterostilbene (30 mg, 0.11 mM)) in 1.25 M (2.5 mL) of NaOH. The mixture was stirred at 60° C. for 5 h and after a second addition of 10 mg of acetobromo-α-D-glucose and 1.0 mL of NaOH) the mixture was stirred at 60° C. for additional 5 h. Ethyl acetate was added and the organic phase was washed with water. The crude mixture was purified using flash chromatography eluting with ethyl acetate/hexanes (3:2) and afforded (E)-2-(acetoxy-methyl)-6-(4-(3,5-dimethoxystyryl)phenoxy)tetrahydro-2H-pyran-3,4,5-triyl triacetate.

To a solution of (E)-2-(acetoxymethyl)-6-(4-(3,5-dimethoxystyryl)phenoxy)tetrahydro-2H-pyran-3,4,5-triyl-triacetate (100 mg, 0.17 mM) in methanol was added a 0.2M solution of methanolic NaOMe (523 µL). After 2 h stirring at room temperature, Dowex 50W-X8 (H$^+$) resin was added until PH neutral. The resin was filtered off and washed with methanol. The crude mixture was purified using flash chromatography eluting Chloroform/methanol (98:2) and afforded ARS18.

Physical data, including mass spectra and IR spectra measurements were obtained for ARS18.

Example 25

(E)-4-(3,5-dimethoxystyryl)benzenethiol ARS27

A solution of pterostilbene (100 mg, 0.39 mM) dimethyl thiocarbonyl chloride (58 mg, 0.47 mM) trietylamine (109 µL, 0.78 mM) dimethylamino pyridine (4.7 mg, 0.039 mM) in dioxane (10 mL) was refluxed for 30 h. The mixture was poured into water and extracted with ethyl acetate. The solvent was evaporated, the crude mixture was purified by column chromatography eluting with hexanes:ethyl acetate (7:3) and afforded (E)-O-4-(3,5-dimethoxystyryl)phenyl dimethylcarbamothioate.

(E)-O-4-(3,5-dimethoxystyryl)phenyl dimethylcarbamothioate in tetradecane was stirred at 240° C. for 12 h. The mixture was poured into water and extracted with ethyl acetate. The crude mixture was purified by column chromatography eluting with hexanes:ethyl acetate (75:25) and gave (E)-S-4-(3,5-dimethoxystyryl)phenyl dimethylcarbamothioate.

To a solution of (E)-S-4-(3,5-dimethoxystyryl)phenyl dimethylcarbamothioate (50 mg, 0.14 mM) in ethyl ether (10 mL) was added LiAlH$_4$ (6 mg, 0.14 mM) at 0° C. The reaction mixture was stirred at 65° C. for 3 h. The mixture was poured into water (10 mL) and a solution of 1M HCL (10 mL). The crude mixture was purified by column chromatography eluting with hexanes:ethyl acetate (4:1) and gave ARS27.

Physical data, including mass spectra and IR spectra measurements were obtained for ARS27.

Example 26

Synthesis of Pterostilbene

Pterostilbene was synthesized following a published procedure with minor modifications and its structure confirmed by the UV, MS and NMR spectra (FIG. 1).

ARS15: (E)-4-(3,5-dimethoxystyryl)phenol. $^1$H NMR (CDCl$_3$, 400 MHz): δ 3.86 (s, 6H); 5.59 (s, 1H); 6.43 (s, 1H); 6.70 (s, 2H); 6.85 (d, 2H, J=8); 6.92 (d, 1H, J=16); 7.05 (d, 1H, J=16); 7.42 (d, 1H, J=8). $^{13}$C NMR (CDCl$_3$, 400 MHz): δ 55.4 (2 C), 99.7, 104.5 (2 C), 115.7 (2 C), 126.5, 128 (2 C), 128.8, 130.1, 139.7, 155.4, 160.9 (2 C). HRMS: Calc for C$_{16}$H$_{15}$O$_3$ 255.10212. Found 255.10222 (M–H).

Example 27

Effect of Pterostilbene on Aberrant Crypt Foci (ACF) in Rat Colon

Animals and Diets

Weanling male F344 rats were obtained from Charles River Breeding Laboratories (Kingston, N.Y.). All experimental diets were purchased from Research Diets (New Brunswick, N.J.) and stored at 4° C. All animals were randomly distributed by weight into control and experimental groups and housed in plastic cages with filter tops (three per cage) under controlled conditions of a 12-hr light and dark cycle, 50% humidity and 21° C. temperature. Animals had access to food and water at all times. Food cups were replenished with fresh diet two times weekly.

Experimental Procedure

Beginning at 5 weeks of age, all rats were fed the modified American Institute of Nutrition-76A (AIN-76A) diet. At 7 weeks of age, the animals were given s.c. injections of azoxymethane (AOM) (CAS no. 25843-45-2, Ash Stevens, Detroit, Mich.) once weekly for 2 weeks at a dose rate of 15 mg/kg body weight. One day after the second AOM injection, groups of animals (n=9 per group) were maintained on AIN-76A diet alone and AIN-76A diet containing 40 ppm pterostilbene. Dose selection of pterostilbene was based on the inventors' earlier study that 25 mg pterostilbene/kg diet lowered plasma cholesterol and lipoproteins in hypercholesterolemic hamsters. See, e.g., U.S. Application Publication No. US 2006-0057231 A1.

On the average, the animal consumed about 0.6 mg pterostilbene per day. All rats were weighed once weekly until termination of the study at 8 weeks after the second AOM treatment were sacrificed by CO$_2$ asphyxiation. After laparotomy, the entire stomach, small intestine, and large intestine were resected. The organs were opened longitudinally, and the contents were flushed with normal saline.

Aberrant Crypt Foci (ACF) Analysis

For the ACF analysis, the colons were fixed flat between two pieces of filter paper in 10% buffered formalin for a minimum of 24 hr. The colons were then cut into 2-cm segments, starting at the anus. They were stained with 0.2% methylene blue in Krebs-Ringer solution for 5-10 min, and were then placed mucosal side up on a microscope slide and observed through a light microscope. ACF were counted and recorded according to standard procedures that are being used routinely in the laboratory. Aberrant crypts were distinguished from the surrounding normal crypts by their increased size, the significantly increased distance from lamina to basal surface of cells, and the easily discernible pericryptal zone. The parameters used to assess the aberrant crypts were their occurrence and multiplicity. Crypt multiplicity was determined as the number of crypts in each focus. Multicrypts were categorized as containing up to four or more aberrant crypts/focus.

Statistical Analysis

Total number of ACF/colon and multiple aberrant crypts/focus were counted and the data were analyzed by Student's t-test. The PCNA labeling index (PI) was calculated as the [(number of positive cells)/(total number of cells)]×100 for each field which is averaged to get the PI for each section. The significance of treatment between the groups was analyzed by Student's t-Test.

General Observations

Body weights of animals fed the experimental diet containing pterostilbene were comparable to those fed the control diet throughout the study, indicating that the dose of pterostilbene used did not cause any overt toxicity (data not shown).

Efficacy of Pterostilbene on ACF Formation.

ACF were predominantly observed in the distal colon. Endpoints used in this study were the occurrence of total ACF as well as multicrypt clusters (more than 4 crypts/focus) of aberrant crypts (Table 1). Rats treated with AOM and fed the pterostilbene diet showed a significantly lower number of total ACF/colon compared to those fed the control diet (57% inhibition, p<0.001). The incidence of multiple aberrant crypts/focus was also significantly inhibited in rats fed the pterostilbene diet as compared to those fed the control diet (29% inhibition, p<0.01).

TABLE 1

Inhibitory effects of dietary pterostilbene on azoxymethane-induced aberrant crypt foci (ACF) in male F344 rats.

| Experimental diets | ACF/colon[§] | >4 ACF/colon[§] |
|---|---|---|
| Control diet (AIN-76A) | 273 ± 17 | 35.6 ± 8.3 |
| 40 ppm pterostilbene | 117 ± 12* | 25.1 ± 5.6** |

[§]Mean ± S.D. (n = 9)
*Significantly different from the control diet group, p < 0.001 by Student's t-test.
**Significantly different from the control diet group, p < 0.01 by Student's t-test.

Example 28

Effect of Pterostilbene on the Amount of Inflammatory and Proliferative Markers in Colon Cells Materials and Methods Animals were treated as described in Example 27. Colon samples from each group were harvested at autopsy and fixed in 10% formalin for 24 hr. They were sectioned into 8 to 10 segments, paraffin embedded, and microtomed into 4 μm thick tissue sections. The slides were incubated overnight at room temperature with antibody to proliferating cell nuclear antigen (PCNA) (1:1000 diluted, BD Pharmingen, San Diego, Calif.), iNOS (1:100 diluted, Santa Cruz Biotechnology, Santa Cruz, Calif.), or mucin MUC2 (1:250 diluted, Santa Cruz Biotechnology, Santa Cruz, Calif.).

The slides were incubated with the biotinylated secondary antibody, and then with avidin/biotinylated peroxidase complex for 30 min at room temperature (Vector Labs, Burlingame, Calif.), and were incubated with 3'-diamino-benzamine (DAB) substrate. The sections were then counterstained with Modified Harris Hematoxylin. The images were taken randomly at 400× using Zeiss AxioCam HRc camera fitted to a Zeiss Axioskope 2 Plus microscope. A positive reaction is noted by a reddish brown precipitate in the nucleus for PCNA, in the cytoplasm for iNOS or in the colon crypts for mucin MUC2.

PCNA Staining of Colons and Cell Counting

Proliferating cell nuclear antigen (PCNA) was evaluated as a marker for cell proliferation in the colon specimens. Sections of colon samples from the control group or pterostilbene fed group are shown (FIG. 1). The PCNA staining of the normal mucosa of colon tissue was much stronger in control group (A) than in the pterostilbene-fed group (B). The PCNA labeling index is also shown in FIG. 1. The colon sections from the control group showed a higher number of positive cells than those from pterostilbene-treated rat colons. PCNA positive cells (%) of colon tissue in the control group were 56.6±2.8%, whereas PCNA positive cells (%) from pterostilbene fed group were 44.2±2.9%. The two groups were significantly different (p<0.01).

Inducible Nitric Oxide Synthase (iNOS) Staining of Colons

Figure 2A:
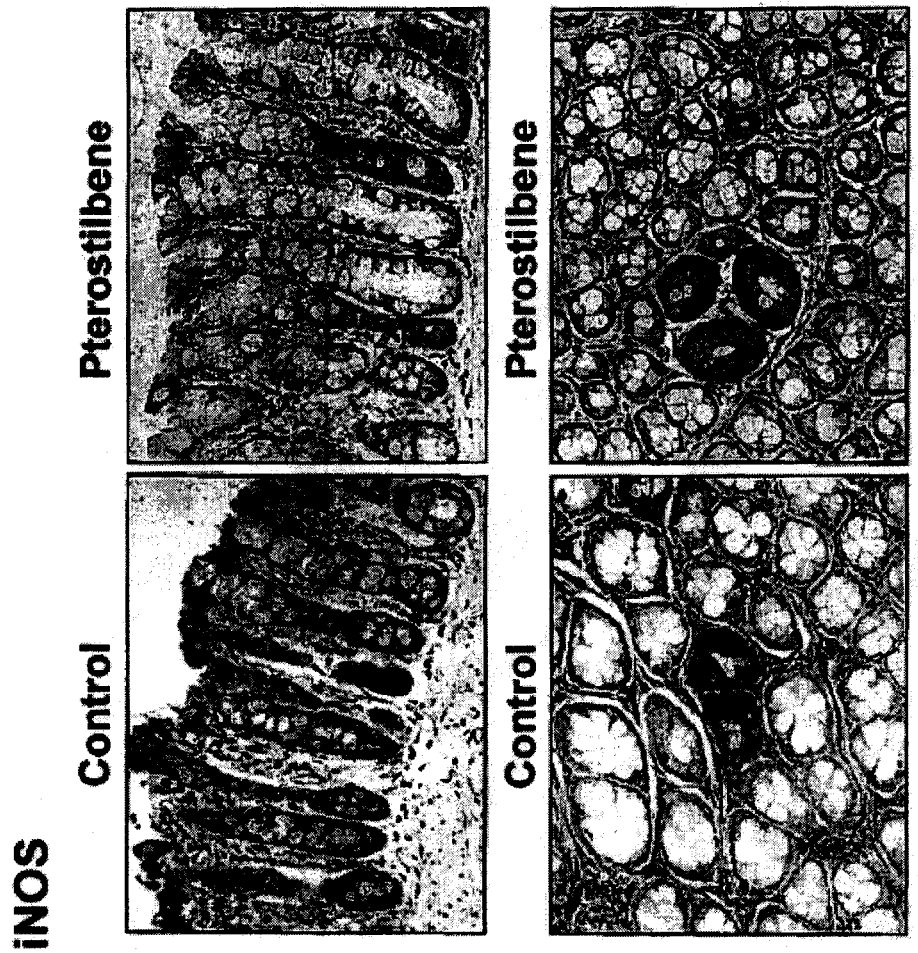
FIG. 2 illustrates labeling for iNOS (A) and mucine (B) in colons of rats fed with control diet and pterostilbene-containing diet.

Since the inhibition of inflammatory genes such as iNOS may contribute to the suppression of ACF formation in colon carcinogenesis, it was important to determine whether pterostilbene might inhibit AOM-induced iNOS in the colon. The iNOS expression was evaluated as a marker for inflammatory response in the colon specimens. Two independent sections of colon samples from control group or pterostilbene fed group are shown (FIG. 2A).

The iNOS staining of the colon tissue was stronger in control group than in pterostilbene-fed group. The colon sections from the control group showed higher staining of iNOS in the cytoplasm than those from pterostilbene-treated rat colons. The inventors found that ACF with moderate dysplasia from the control group displayed stronger cytoplasmic staining, whereas ACF with moderate dysplasia from pterostilbene-fed group showed weak cytoplasmic staining.

iNOS is overexpressed in colonic tumors of humans and also in rats treated with a colon carcinogen, AOM. Using the same animal model of AOM-induced tumors in F344 rats, the selective iNOS inhibitor L-$N^6$-(1-iminoethyl)lysine tetrazoleamide was previously shown to significantly suppress AOM-induced colonic ACF at a higher dose of 100 ppm. Another report of a selective iNOS-specific inhibitor, S,S'-1, 4-phenylene-bis(1,2-ethanediyl)bis-isothiourea (PBIT), showed the inhibitory effects against formation of AOM-induced colonic ACF. The inhibitory effect of 100 ppm of an iNOS inhibitor, ONO-1714 ([1S,5S,6R,7R]-7-chloro-3-imino-5-methyl-2 azabicyclo[4.1.0]heptane hydrochloride), on AOM-induced rat colon carcinogenesis also has been reported with 100 ppm.

In the instant study, pterostilbene showed inhibition of ACF (57% inhibition) at 40 ppm. These data also show that the suppression of ACF formation is mediated through the inhibition of colonic cell proliferation and iNOS expression. The exact mechanism by which pterostilbene reduces cell proliferation and iNOS expression is yet to be established.

The precise pathological functions of iNOS in colorectal cancer are more difficult to specify. Recent reports suggest that iNOS may contribute to tumor development or acceleration of progression stage and that the expression of iNOS is markedly elevated in rat colon cancers induced by AOM. In addition, the detection of iNOS in most adenomas and dysplastic ACF has been reported, suggesting that iNOS plays an important role in colon carcinogenesis. The inhibition of carcinogenesis by pterostilbene underscores that iNOS plays a role in tumorigenesis. The present results suggest that the suppression of iNOS activity by pterostilbene in the instant study may lead to down-regulation of formation of pro-inflammatory cytokines.

On the basis of data presented here, it is likely that naturally occurring iNOS inhibitors may be potential chemopreventive agents. The results of the present study provide evidence that natural products present in fruits, as exemplified by pterostilbene, are of great interest and offer alternatives for the prevention of colon cancer.

Increased Staining of Mucin MUC2 in the Colons by Pterostilbene.

Figure 2B:
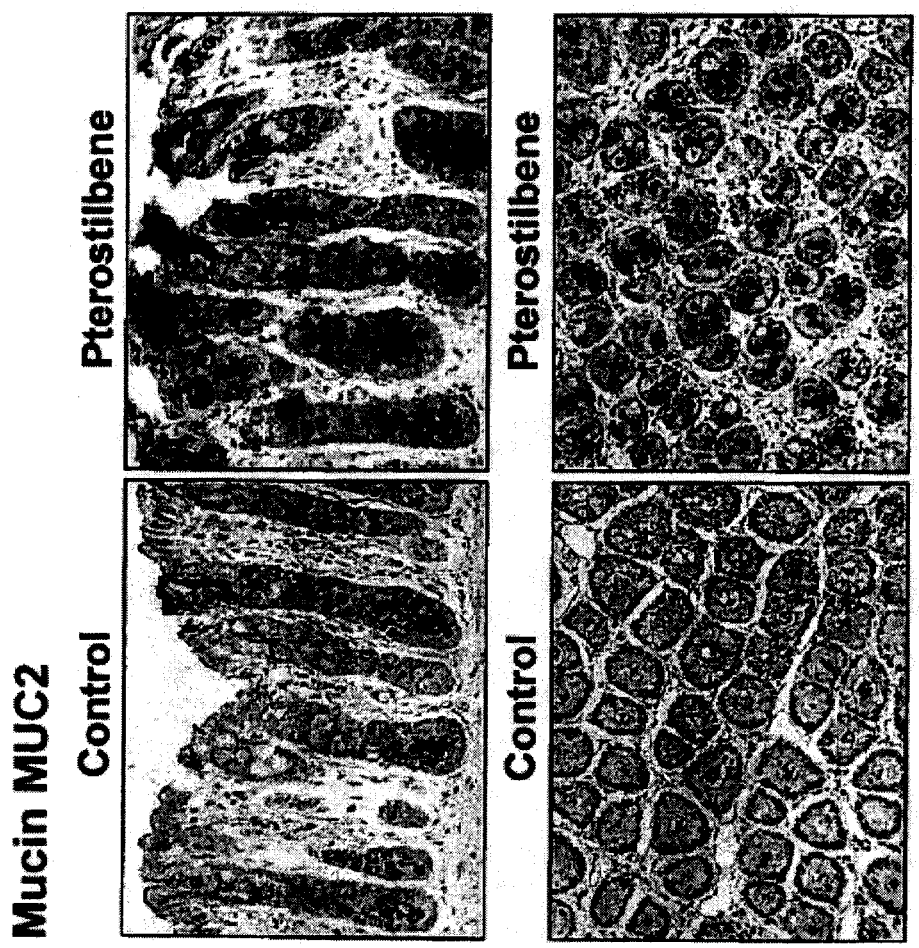

MUC2 is the structural component of the colonic mucus layer which is critical for colonic protection. The colon mucosa from the AOM-treated control group showed little expression of mucin MUC2. However, there was abundant secretion of mucin MUC2 from goblet cells lining the colonic crypts in the pterostilbene-fed group. The staining of en face preparation is also shown in FIG. 2B.

Mucins are secreted gastrointestinal proteins that protect underlying intestinal epithelium and mucin MUC2 is critical for colonic protection. Expression of mucin MUC2 is lowered in inflammatory bowel disease and reports have implicated mucin MUC2 in the suppression of colorectal cancer. The finding that mucin MUC2 expression is higher in pterostilbene-fed group than the control group, provides evidence that pterostilbene may maintain the normal function of the colon and protect colonic mucus layer.

Example 29

Effect of Pterostilbene on iNOS Protein Expression in a Colon Cancer Cell Line

Figure 3:
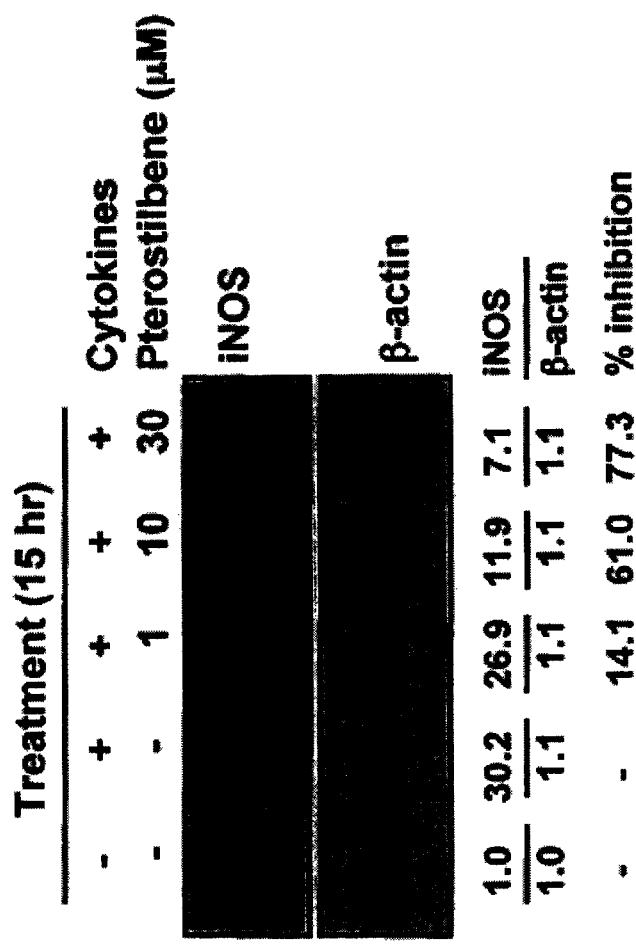
FIG. 3 illustrates inhibition of cytokine-induced iNOS by pterostilbene.

As shown in FIG. 3, pterostilbene inhibited the induction of iNOS protein expression in a colon cancer cell line in vitro. When HT-29 human colon adenocarcinoma cells were treated with cytokine mixtures (IFN-γ, TNF-γ, and LPS, each at 10 ng/ml) for 15 hr, there was a great induction of the synthesis of iNOS protein. When pterostilbene was given together at 1, 10, or 30 µM concentrations, pterostilbene inhibited the induction of iNOS protein expression dose-dependently (14, 61 and 77% inhibition of iNOS expression) in HT-29 cells.

Example 30

Figure 4:
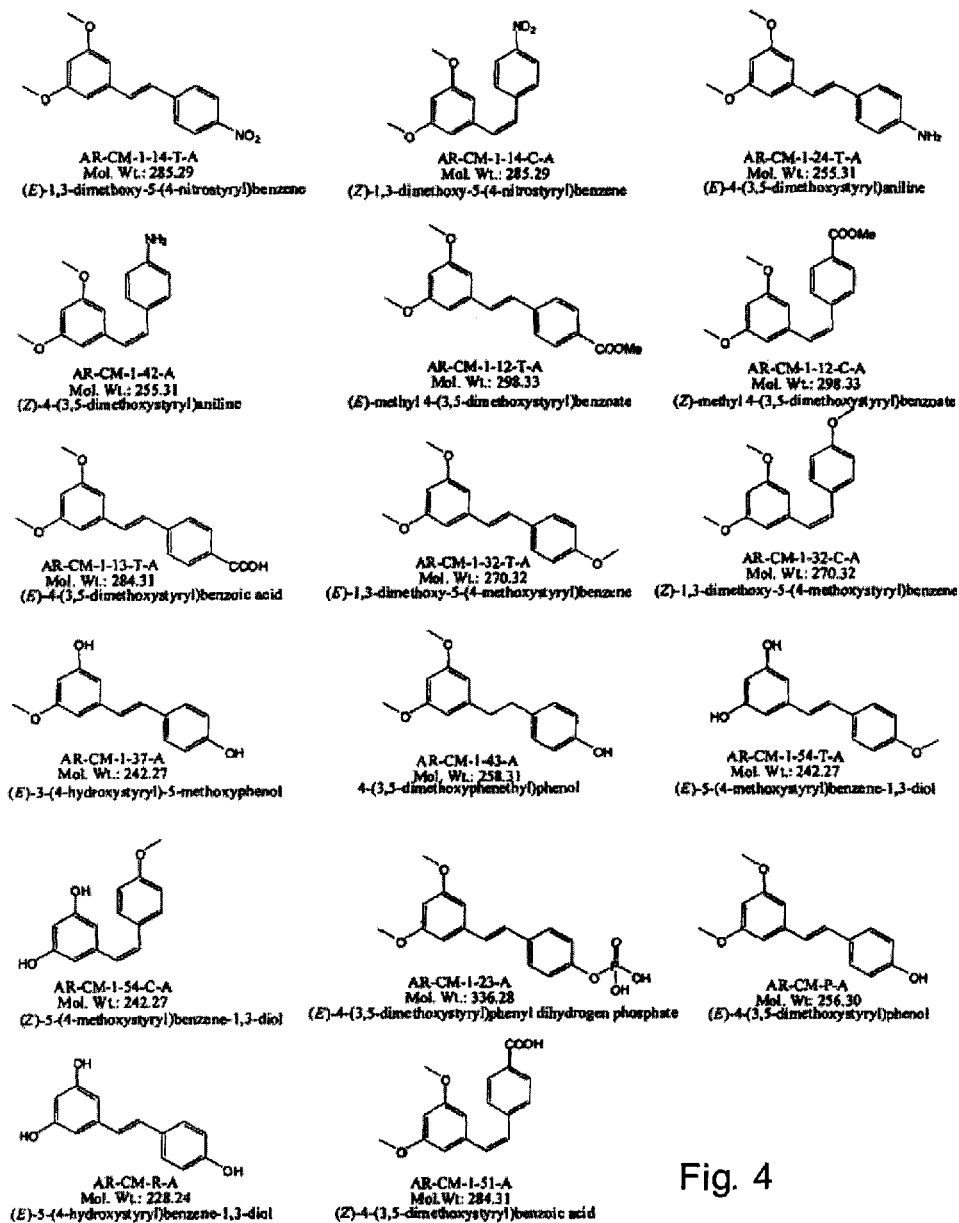
FIG. 4 is an illustration of formulae of selected stilbenes used for some experiments of the instant invention.

Effect of Pterostilbene Analogs on iNOS Protein Expression in a Colon Cancer Cell Line To further investigate the role of stilbenes in cancer treatment or prevention, stilbenes illustrated in FIG. 4 were used. The abbreviations for these stilbenes are provided in FIG. 5.

HT-29 human colon adenocarcinoma cells were grown in 10% FBC/DMEM. Cells (about 600,000 cells/well) were plated in 6-well plate and treated with stilbene analogs shown in FIG. 4 (each at 10 µM) for 15 hours together with cytokine mixture comprising TNF-a, IFN0g, and LPS (each at 10 ng/ml). Cell lysates were prepared and subjected to Western Blot analysis.

Figure 6:
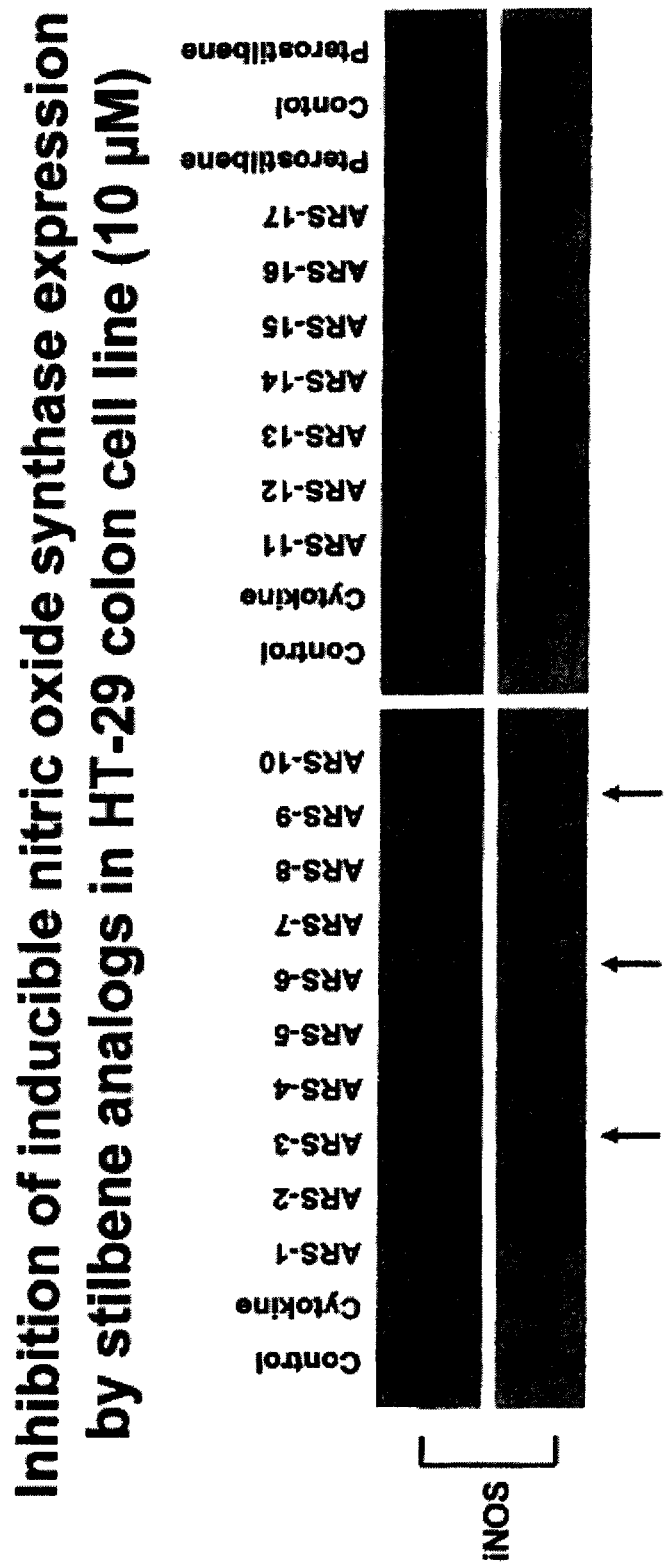
FIG. 6 illustrates inhibition of inducible nitric oxide synthase (iNOS) by stilbenes of FIG. 4.

The mixture of cytokines induced the amount of iNOS. This induction of iNOS protein expression was inhibited by selected stilbenes, most notably, ARS-3, ARS-6, and ARS-9 (FIG. 6).

Example 31

Inhibition of Cell Proliferation in a Colon Cancer Cell Line by Pterostilbene Analogs The stilbenes illustrated in FIG. 4 were also used to investigate their ability to inhibit cell proliferation in HT-29 cell line. In this experiment, HT-29 cells (20,000 cells/well in 24-well plate) were treated with the respective stilbenes (each used either at 30 µM or 3 µM) in 10% FBS/DMEM for three days. [$^3$H]Thymidine incorporation assay was performed to determine growth inhibitory effects of the stilbenes.

Figure 7:
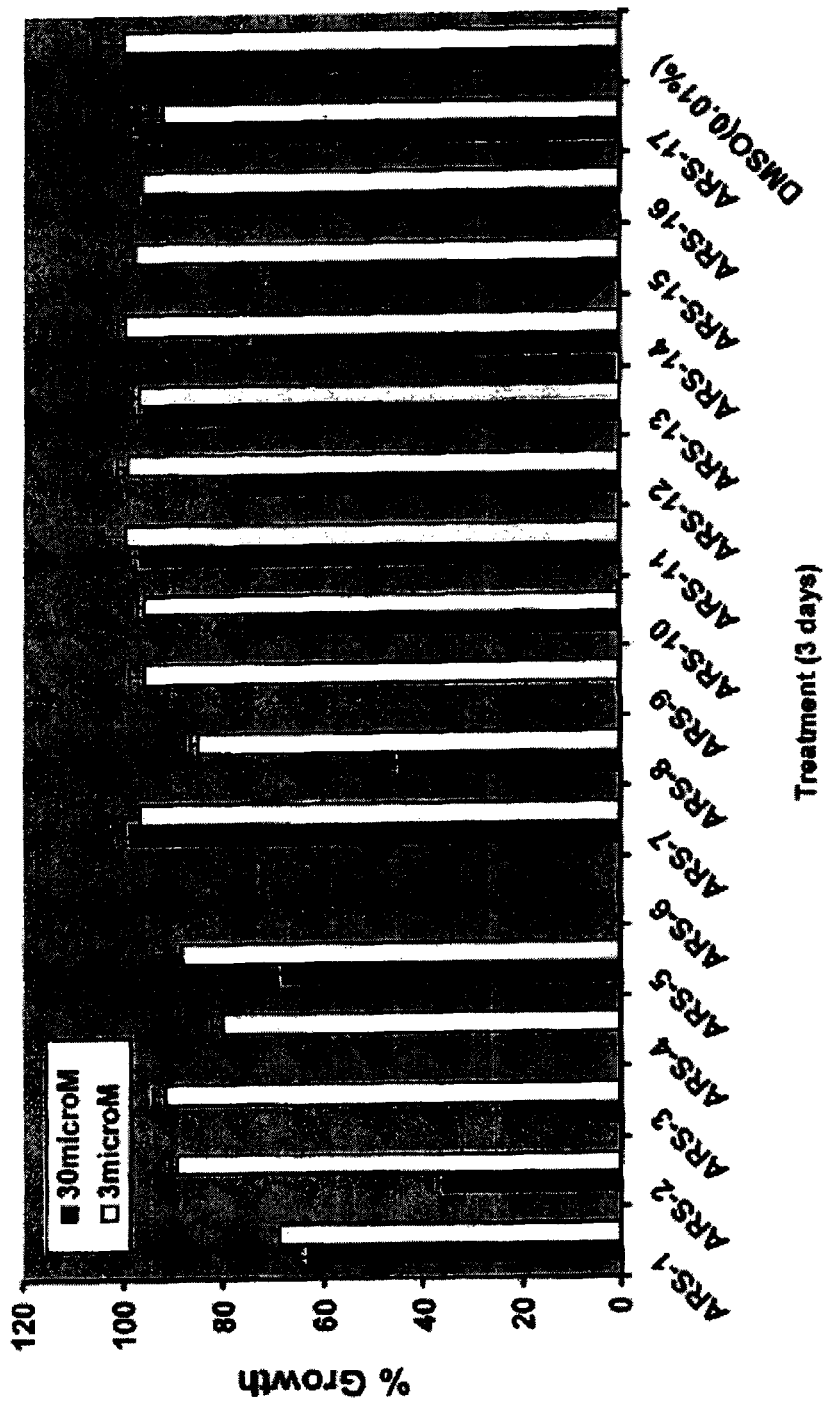
FIG. 7 illustrates the effect of stilbenes of FIG. 4 on growth of HT-29 colon cancer cell line.

The results of these experiments are shown in FIG. 7. At 30 µM, ARS-2, ARS-3, ARS-4, ARS-6, ARS-8, ARS-9, and, to a lesser extent, ARS-1, ARS-5, ARS-10. ARS-12, ARS-14, and ARS-15 inhibited proliferation of HT-29 cells. At 3 µM, ARS-6 had the most pronounced effect.

These data indicate that stilbene analogs are attractive candidates for treatment and prevention of colon cancer.

Example 32

Effect of Pterostilbene on Cell Proliferation in a Colon Cancer Cell Line

Reagents

Pterostilbene was synthesized at the National Products Utilization Research Unit, USDA (Mississippi) (purity >99.9%). The compound was dissolved in dimethyl sulfoxide (DMSO) and the final concentration of DMSO used in the experimental set up was 0.1% or less. The controls were run with DMSO alone in all experiments. Recombinant human IFN-γ and TNF-α were purchased from R & D Systems, Inc. (Minneapolis, Minn.), and lipopolysaccharide (from *Escherichia coli* 0111:B4 γ-irradiated) was purchased from Sigma (St. Louis, Mo.). The kinase inhibitors, PD98059, SB203580, SP60025, LY294002, and Akt inhibitor, were obtained from Calbiochem (San Diego, Calif.).

Cell Culture

Human colon carcinoma cell lines HT-29 was obtained from the American Type Culture Collection (Manassas, Va.). The cells were maintained in Dulbecco's modification of Eagle's medium (DMEM) supplemented with 10% FBS and 1% penicillin/streptomycin at 37° C. and 5% $CO_2$. The cytokine mixture, consisting of 10 ng/ml of TNF-α, IFN-γ and LPS, was used to induce iNOS and COX-2, unless otherwise mentioned. The cells were treated with the test compound either alone or in combination with cytokines for different time intervals and harvested for protein or RNA.

Measurement of Cell Proliferation by [$^3$H]Thymidine Incorporation

HT-29 cells were plated at a density of 20,000 cells/well in a 24 well plate and treated with varying concentrations of pterostilbene for a period of 1, 2 or 3 days at 37° C. Before harvest, the cells were incubated with 1 µCi [$^3$H]thymidine for 4 h at 37° C. and were washed with phosphate buffered saline. The cells were precipitated with cold 10% trichloroacetic acid for 10 min and solubilized with 0.5 ml solubilization buffer (0.2 M NaOH, 40 μg/ml salmon sperm DNA) for 2 h at room temperature. The lysate was transferred to 5 ml Ecolume and the [3H]thymidine incorporated into the DNA of HT-29 cells was determined using a scintillation spectrometer (Beckman Coulter, Fullerton, Calif.).

Figure 8:
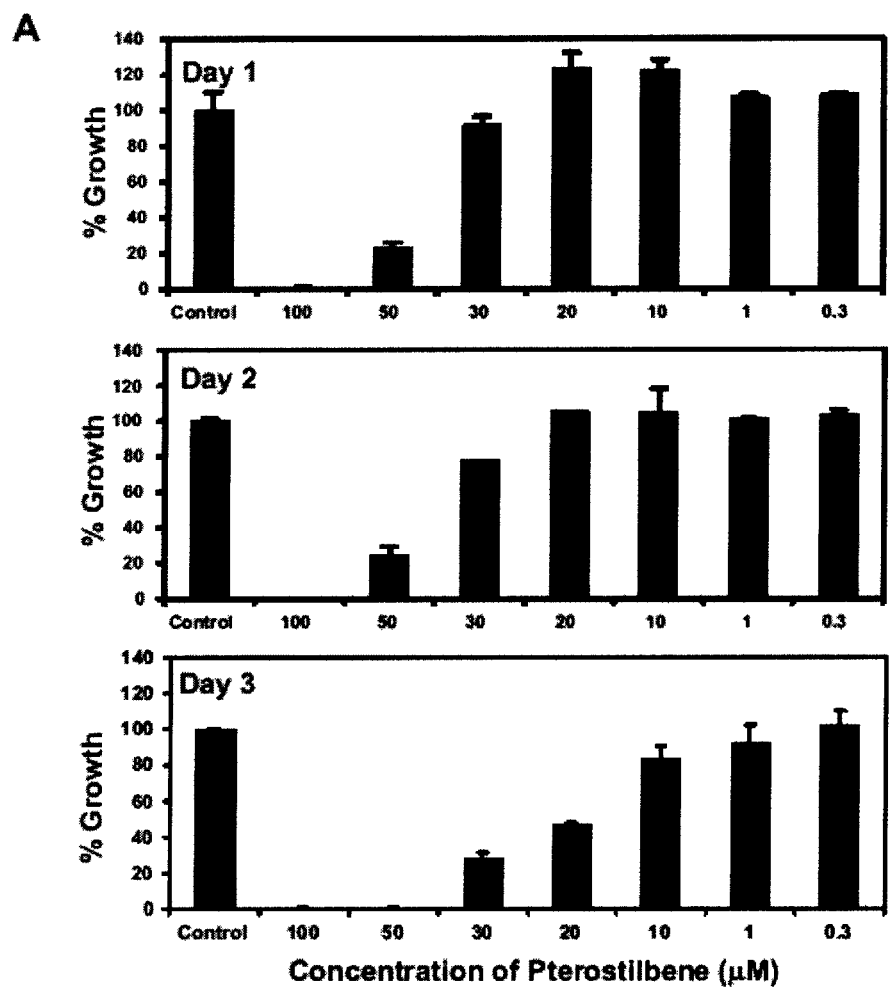
FIG. 8 illustrates the effect of pterostilbene on growth of HT-29 colon cancer cell line.
Figure 8:
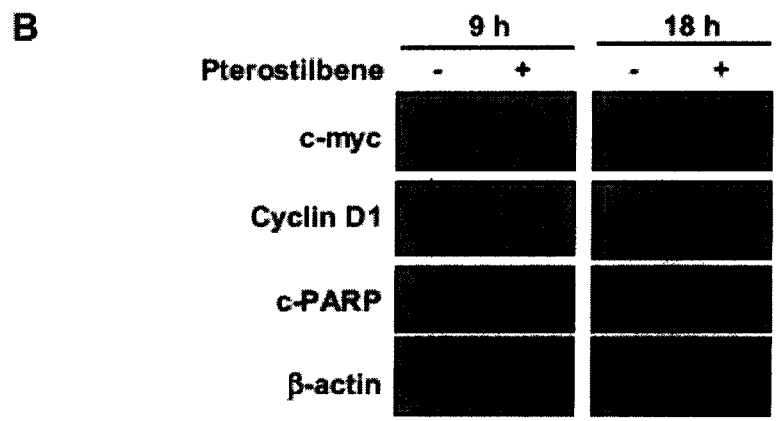

The growth inhibitory effect of pterostilbene in HT-29 cells was tested. The cells were incubated with different concentrations of pterostilbene for 1, 2 and 3 days, and cell proliferation was estimated by measuring [$^3$H]thymidine incorporated into DNA. As illustrated in FIG. 8A, pterostilbene reduced DNA synthesis in a dose-dependent manner with 71±3% inhibition at a concentration of 30 μM at 3 days. The longer incubation with pterostilbene gave the strongest growth inhibitory effect (FIG. 8A). In order to evaluate whether pterostilbene potentiates cell cycle arrest or apoptosis in HT-29 cells, the effect of pterostilbene on the proteins regulating the cell cycle and/or apoptosis pathways was examined. Cells treated with pterostilbene for 9 h or 18 h were harvested and protein samples were analyzed by Western blotting (FIG. 8B).

Pterostilbene was effective in reducing c-myc and cyclin D1 levels, especially at 9 h. However, pterostilbene showed no induction of p21 and p27, which belong to CIP-KIP family of cyclin dependent kinase inhibitors (data not shown). As a marker for the induction of apoptosis, the level of cleaved PARP was determined. The treatment with pterostilbene for 9 h or 18 h increased the level of cleaved PARP, which serves as evidence that pterostilbene induces apoptosis in HT-29 cells (FIG. 8B).

Example 33

Cytokine Induction of iNOS and COX-2 in HT-29 Cells

Western Blot Analysis

The cell culture conditions and the reagents used in this example were described in Example 32. Whole cell extracts were collected after the various treatments and analyzed by western blotting. The protein samples were separated on 4-15% SDS-PAGE gels (Biorad, Hercules, Calif.) followed by transfer to a polyvinylidene fluoride membrane. The membranes were blocked with 5% milk in Tris buffer for 1 h and then incubated with the appropriate primary antibody solutions overnight at 4° C. The membranes were washed with Tris buffer, and incubated with horseradish peroxidase conjugated secondary antibody solutions for 1 h at room temperature.

The protein bands were visualized using a chemiluminescence based kit from Amersham Biosciences (Buckinghamshire, UK). The primary antibodies against iNOS, COX-2, IκBα, cyclin D1, c-myc (Santa Cruz Bio-technology, Santa Cruz, Calif.), phospho-STAT3, phospho-Erk1/2, phospho-JNK1/2, phospho-p38, phospho-Akt, phospho-ATF2, phospho-Elk1, PARP (Cell Signaling Technology Inc., Beverly, Mass.) and actin (Sigma, St. Louis, Mo.) and secondary antibodies (Santa Cruz Biotechnology, Santa Cruz, Calif.) were used for probing the abundance of the target protein in the samples.

Figure 9:
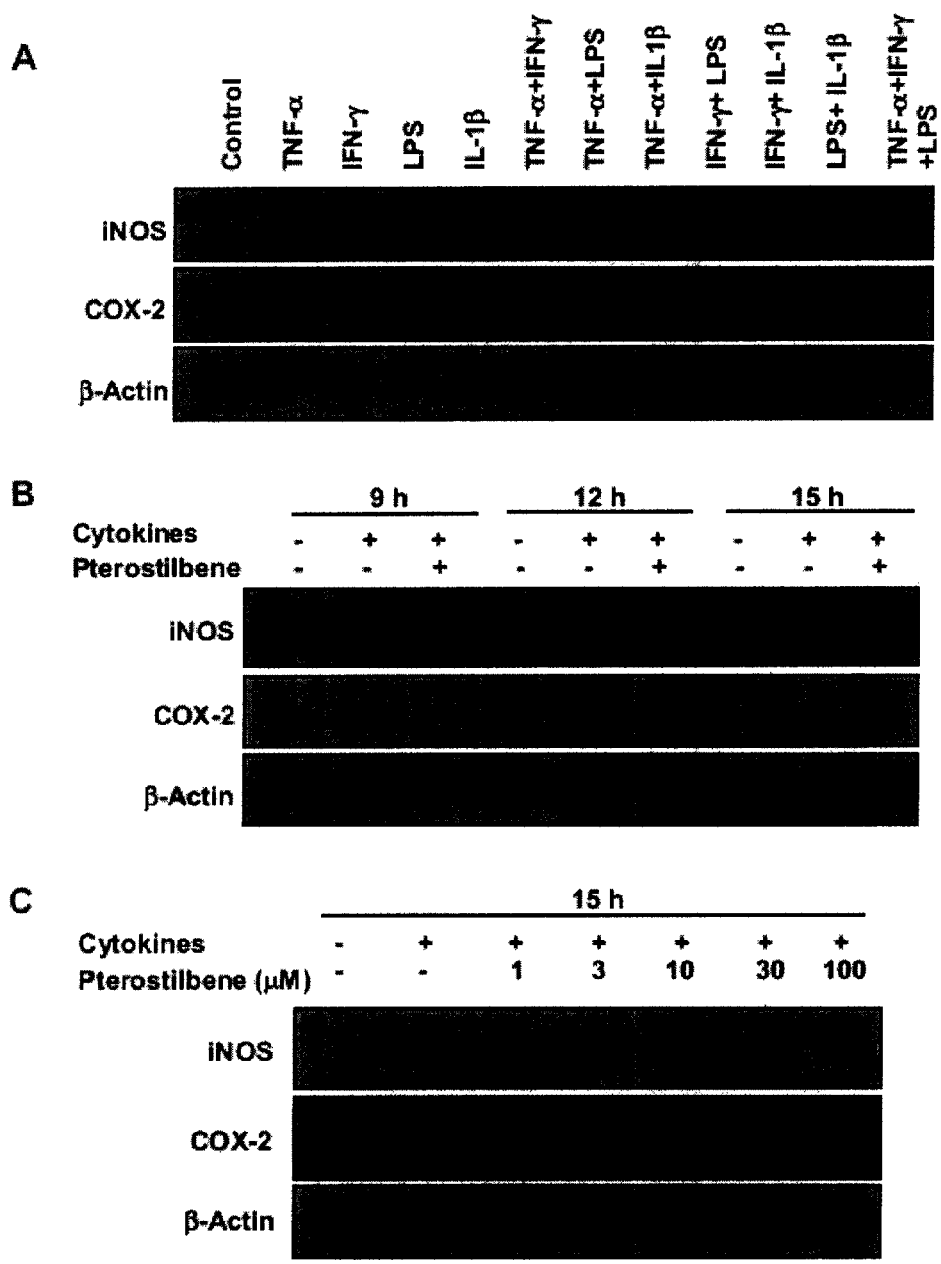
FIG. 9 demonstrates that iNOS and COX-2 are induced differently by various cytokines in HT-29 cells (A), that this induction is inhibited by pterostilbene (B), and that the inhibition is dose-dependent (C).

Induction of iNOS and COX-2 has been reported to be maximal with a combination of cytokines for a number of cell lines. HT-29 cells were treated with TNF-α, IFN-γ, LPS and IL-1β either alone or in combination for 15 h (FIG. 9A). Addition of the cytokines individually to HT-29 cells did not cause a noticeable induction of iNOS. Although the addition of IFN-γ plus LPS caused a strong induction, even stronger induction of iNOS amongst the combinations tested was exhibited by a triple combination of TNF-α, IFN-γ and LPS. COX-2 was induced by TNF-α, LPS or IL-1β individually, and TNF-α was the most potent inducer.

The combination of TNF-α with either IL-1β or LPS yielded the strongest induction. The triple combination of TNF-a, IFN-γ and LPS caused a moderate induction of COX-2. Since the triple combination induced both iNOS and COX-2, this combination was selected for additional studies. Apart from HT-29 cells, other colon carcinoma cells were evaluated for induction of iNOS and COX-2 by TNF-α, IFN-γ and LPS at 10 ng/ml each (data not shown). These cell lines include HCT-116, DLD-1 (with no observable induction of iNOS and COX-2), Caco-2 (with a slight induction of iNOS and COX-2) and LoVo (with good induction of iNOS, but it had relatively high basal level of COX-2 and the cytokines failed to cause a further increase).

Example 34

Effect of Pterostilbene on Cytokine Induction of iNOS and COX-2

The materials and methods for this example have been described in Examples 32 and 33. To determine the kinetics of induction of iNOS and COX-2 in HT-29 colon cancer cells, the cells were treated with the cytokine mixture of TNF-α, IFN-γ and LPS for periods of 9, 12 and 15 h. The induction of iNOS was highest at 15 h while the COX-2 level was high at 9-12 h and low at 15 h (FIG. 9B). Similar experiments conducted for 6 and 24 h showed weaker induction of iNOS and COX-2 (data not shown).

These data show that maximal induction of COX-2 occurs earlier than that of iNOS. As also shown in FIG. 9B, pterostilbene at 30 μM markedly blocked the induction of iNOS and COX-2 by the cytokine mixture at each time point. In addition, we determined the effect of treatment of the cells with different concentrations of pterostilbene on the induction of iNOS and COX-2 by the cytokine mixture. Pterostilbene inhibited the induction of iNOS and COX-2 in a dose-dependent manner (FIG. 9C).

Example 35

Pterostilbene Down-Regulation of mRNA Levels of Inflammatory Genes iNOS and Cox-2 and Pro-Inflammatory Cytokines IL-1β and TNF-α

The cell culture conditions and the reagents used in this example were described in Example 32. The gene-mediated expression of iNOS and COX-2 are reported to be regulated at both the transcriptional and translational levels. In order to understand the effect of pterostilbene on cytokine-induced expression of proinflammatory enzymes and cytokines, RNA samples after treatment of HT-29 cells with cytokines and/or pterostilbene were analyzed by quantitative RT-PCR for the induction of mRNA levels of iNOS, COX-2, IL-1β, IFN-γ and TNF-α genes.

Figure 10:
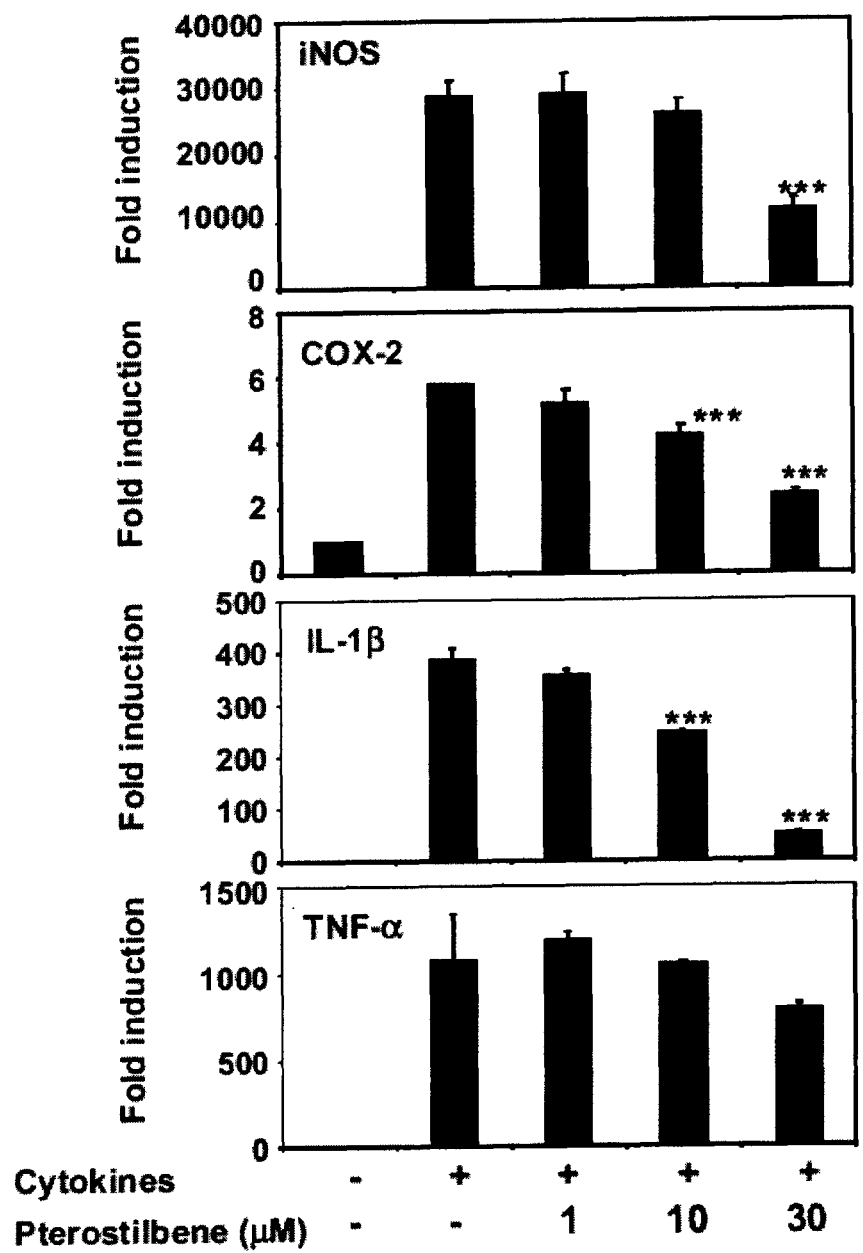
FIG. 10 demonstrates that pterostilbene inhibits cytokine-induced formation of mRNA for iNOS, COX-2, IL-1β, and TNF-α.

Pterostilbene at 10 and 30 μM strongly inhibited iNOS, COX-2, and IL-1β mRNA induction by the cytokine mixture (FIG. 10). Induction of TNF-α mRNA was observed, but pterostilbene showed a weak inhibitory effect (FIG. 10). The mRNA level of IFN-γ induced by the cytokine mixtures was too low to be detected in HT-29 cells (data not shown).

Example 36

Signaling Pathways for Regulating iNOS and Cox-2 Formation in HT-29 Cells

Quantitative Reverse Transcription-Polymerase Chain Reaction (RT-peR) Analysis

To determine the changes of mRNA levels by pterostilbene and cytokines, quantitative RT-PCR analysis was utilized, as described previously (Lee et al., *Mol Pharmacol* 2006; 69(6): 1840-1848). Briefly, the cells were incubated with compounds for indicated period and the cells were then lysed using Trizol to extract RNA. RNA was reverse transcribed into cDNA using a high capacity cDNA archive kit (Applied Biosystems, Foster City, Calif.). The cDNA was used for quantitative PCR which was run on the ABI Prism 700 sequence Detection System. The primers for the iNOS, COX-2, IFN-γ, TNF-α, IL-1β and GAPDH were obtained from Applied Biosystems (Foster City, Calif.).

Figure 11:
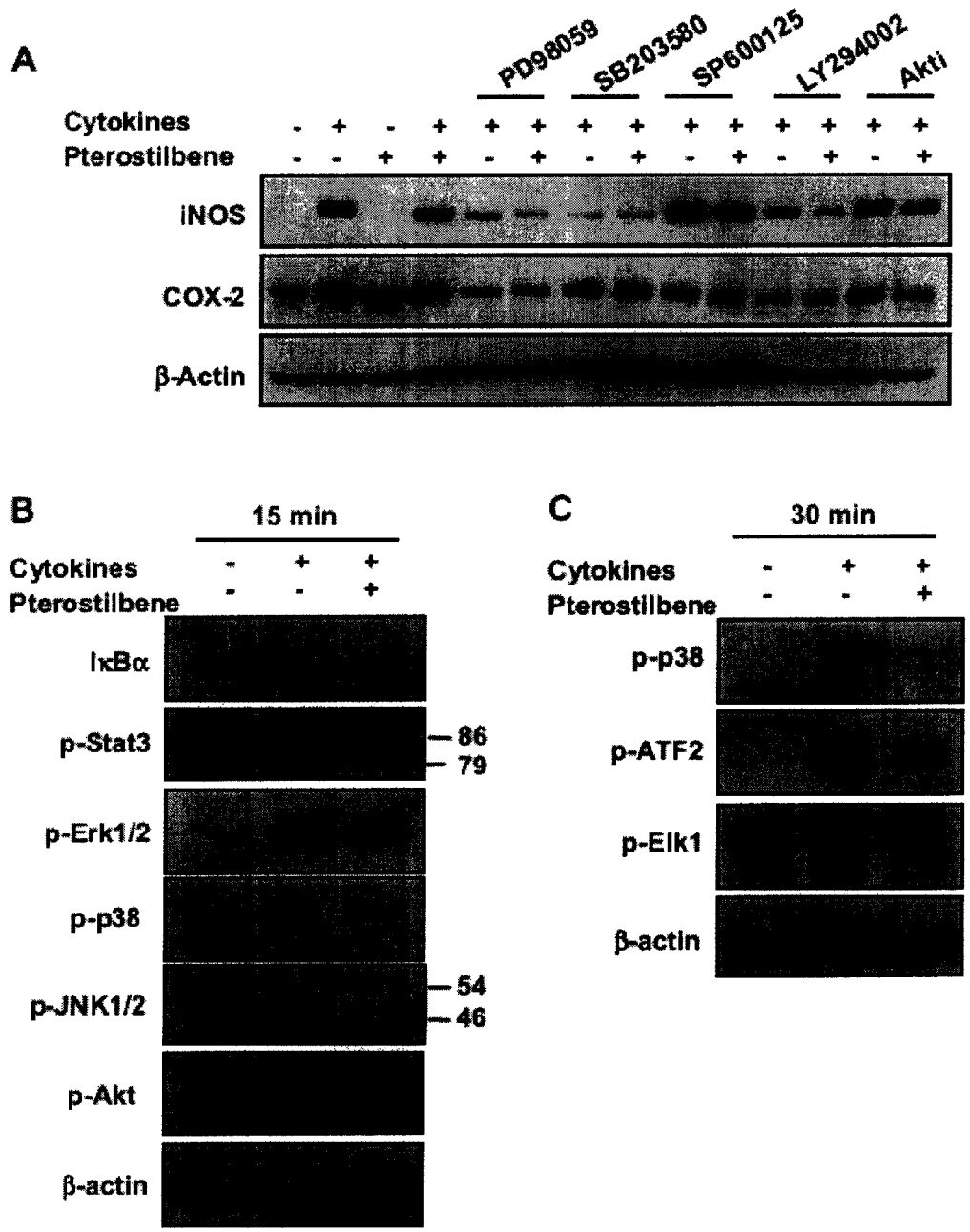
FIG. 11 illustrates the effect of inhibitors of different signaling pathway on the effect of pterostilbene.
Figure 12:
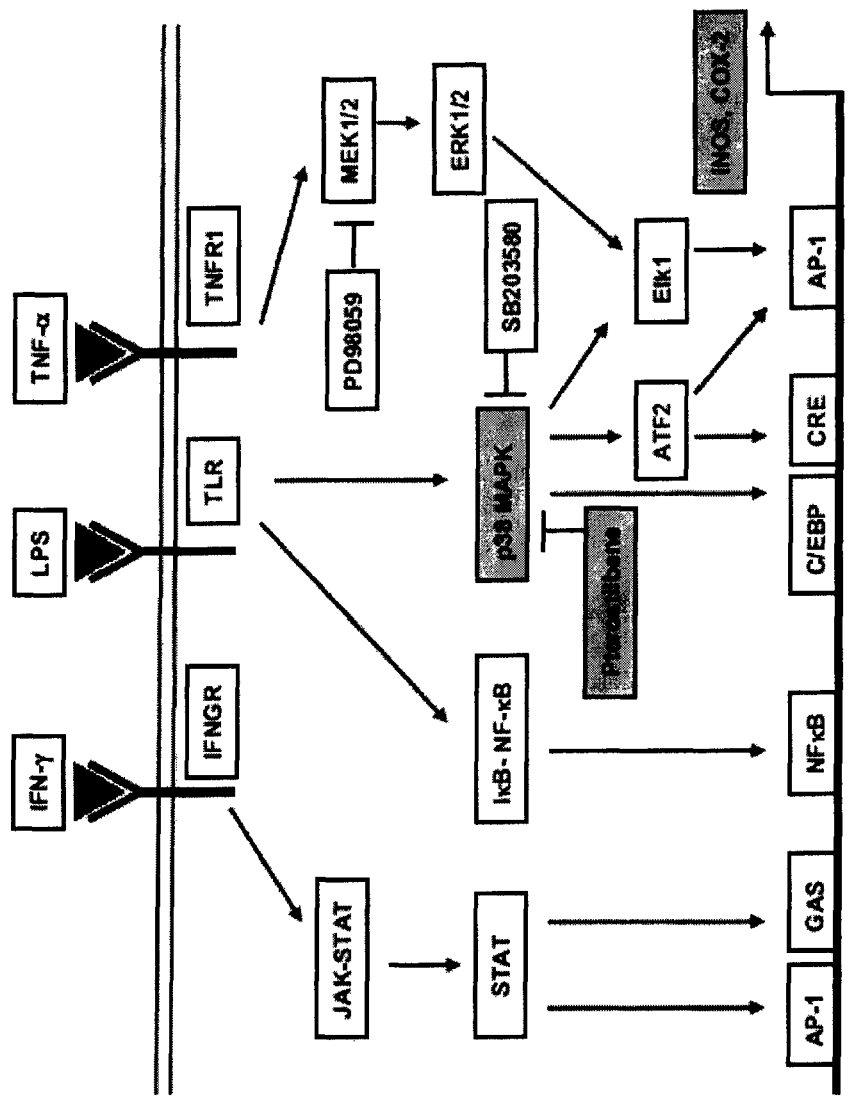
FIG. 12 is an illustration of intracellular signaling mechanisms used by pterosterol.

Cytokines are known to induce iNOS and COX-2 through various signaling pathways. In an attempt to evaluate the role of relevant kinases in the suppression or activation of iNOS and COX-2, pharmacological inhibitors for these kinases were used. HT-29 cells were treated with PD98059 (inhibitor of MEK1/2, upstream kinase of ERK1/2), 58203580 (p38 kinase inhibitor), SP600125 (JNK inhibitor), LY294002 (PI-3-kinase inhibitor) and an Akt inhibitor either with or without pterostilbene (30 μM) for 15 h (FIG. 11A). Interestingly, all the kinase inhibitors tested, except the JNK and AKT inhibitors, reduced the induction of iNOS and COX-2.

The results obtained from pharmacological inhibitors indicate that the ERK1/2, p38 MAPK and the PI-3-kinase pathways may be important for the induction of iNOS and COX-2 in HT-29 cells by the cytokine mixture of TNF-α, IFN-γ and LPS. Treatment of HT-29 cells with pterostilbene along with the inhibitors of MEK and PI-3-kinase further reduced iNOS expression. In studies with kinase inhibitors on iNOS formation in HT-29 colon cancer cells, the p38 inhibitor was by far the most effective, suggesting that p38 is an important target of inflammation in colon cancer and possibly a target for the anti-inflammatory action of pterostilbene. With regard to COX-2 expression, inhibitors of ERK and PI-3-kinase, and to a lesser extent the p38 inhibitor, lowered COX-2 expression.

Example 37

Pterostilbene Down-Regulation of iNOS and COX-2 By Blocking p38 Activation

To elucidate the mechanism responsible for the anti-inflammatory action of pterostilbene, the upstream pathways for iNOS and COX-2 formation were examined. These pathways are activated rapidly after cytokine treatment.

As shown in FIG. 11B, cytokine treatment for a short time (15 min) decreased Iκ Bα levels because IκBα is phosphorylated and degraded to activate the NFκB pathway. Pterostilbene, however, did not block the effects on IκBα induced by the cytokines. The non-involvement of NF-κB was confirmed by examining the nuclear protein levels of the p65 subunit of NF-κB, which remained high and unaltered after the treatment with pterostilbene (data not shown). The significance of the JAK-STAT pathway in HT-29 cells was evaluated by probing for phospho-STAT3. Cytokines activated the STAT pathway, as shown by a strong induction of phospho-STAT3. However, pterostilbene did not alter the level of induced phospho-STAT3 (FIG. 11B).

When the activation of ERK1/2 and p38 kinases by cytokines was determined by measuring the levels of phosphorylated ERK1/2 and p38, the inventors found that pterostilbene did not block ERK1/2 activation but strongly inhibited activation of p38 (FIG. 11B). JNK activation was not noticeable, and there was only a small effect of pterostilbene on p-JNK1/2 protein levels. Interestingly, cytokine treatment or pterostilbene did not change the level of p-Akt, which is the downstream effector of the PI3-kinase pathway (FIG. 11B).

The significance of the transforming growth factor (TGF-β) pathway in down-regulating iNOS expression by pterostilbene was also investigated since TGF-β is a very potent inhibitor of iNOS and cytokines regulate Smad signaling of the TGF-β pathway. However, there was no effect of pterostilbene on activated Smad levels (p-Smad3) or in inducing TGF-β ligands (data not shown).

Example 38

Pterostilbene Inhibition of the Activation of Downstream Targets of p38

Since pterostilbene is effective in down-regulating the cytokine-induced activation of p38, the involvement of pterostilbene on some of the known downstream targets of p38 kinase was further examined. FIG. 11C shows that pterostilbene was effective in inhibiting cytokine-induced activation of ATF2 and Elk-1, which was determined by their phosphorylation. These results further confirm the significance of the inhibitory effect of the p38 pathway as a key target for the anti-inflammatory action of pterostilbene.

The foregoing examples demonstrate the action of pterostilbene, a compound present in blueberries, and analog compounds, on the growth of a human colon adenocarcinoma cell line, HT-29. Pterostilbene inhibited the growth of HT-29 cells and altered markers of cellular proliferation and apoptosis, as shown by lower protein levels of c-myc and cyclin D1 and an increased level of cleaved PARP in pterostilbene treated cells.

These data are consistent with the results of a recent study indicating that pterostilbene or resveratrol induces apoptosis and down-regulates genes that are directly involved in cell proliferation including cyclin D1 in vivo and in vitro. See, Schneider et al., *Nutr. Cancer*, 39(1), 102-107 (2001), Ferrer et al., *J. Biol.*, 282(5), 2880-2890 (2007) and Notas et al., *Biochimica. et Biophys. Acta (BBA)—General Subjects*, 1760(11), 1657-1666 (2006).

TNF-α, IFN-γ, IL-1β and LPS are effective inducers of the expression of inflammatory genes in macrophages and epithelial cells, although expression levels vary with cell type. The human iNOS gene was first cloned from hepatocytes that were induced with a combination of TNF-α, IFN-γ and IL-1β for maximal gene expression. One of the plausible synergies between cytokines is observed because IFN-γ activation of the human iNOS promoter requires a functional AP-1 regulatory region, which in turn needs to be induced by TNF-α or LPS.

In the instant studies with HT-29 cells, a triple combination of TNF-α, IFN-γ and LPS resulted in a marked induction of iNOS and COX-2 (FIG. 9A), and pterostilbene reduced the induction of iNOS and COX-2 in a dose-dependent fashion (FIG. 9C). Quantitative RT-PCR data show that the regulation of iNOS and COX-2 occurs at the transcriptional level with pterostilbene effectively down-regulating the cytokine induction of iNOS and COX-2 mRNA (FIG. 10).

Cytokines, such as TNF-α and IL-1β, are known to trigger a series of inflammatory responses including the induction of inflammation genes, and intestinal inflammation was shown to be reduced by receptor antagonists to IL-1β. In our study with HT-29 cells, treatment with a mixture of cytokines induced mRNA synthesis for pro-inflammatory cytokines, such as IL-1β, and this was significantly inhibited by pterostilbene. These results underscore the anti-inflammatory potential of pterostilbene.

The regulation of iNOS and COX-2 is mediated by the multiple pathways, which vary with cell type and cytokines used. The involvement of NF-κB, AP-1, MAPKs and JAK-STAT in the expression of these genes has been evaluated for a variety of compounds with anti-inflammatory potential. Reservatrol, which is structurally similar to pterostilbene, reduced iNOS and COX-2 induction in rat glioma cells and inhibited iNOS induction by LPS in macrophages by reducing NF-κB. Down-regulation of c-jun and c-fos (components of AP-1), NF-κB, and decreased phosphorylation of ERK and p38 have been implicated in the effect of resveratrol to lower COX-2 in mouse skin.

However, the data of the instant application with pharmacological inhibitors and evaluation of phosphorylation states for the kinases suggest that p38 MAP kinase is a major signaling pathway inhibited by pterostilbene, and this effect is responsible for the inhibitory effect of pterostilbene on the expression of iNOS and COX-2 in HT-29 cells. Among the different MAPKs, p38 has well been associated with inflammation since it was first identified as an IL-1 and LPS activated kinase. p38 MAP kinase has also been implicated in iNOS expression in mouse astrocytes and LPS stimulated macrophages. The inventors' finding is in line with the fact that promoter regions of iNOS and COX-2 contain consensus binding sites for NFκB, AP-1, CRE and C/EBP, to name a few, many of which act as substrates of p38 MAPK.

Taken together, the data of the instant disclosure provide a possible model of regulation of iNOS and COX-2 by pterostilbene in HT-29 colon cancer cells, which is schematically summarized in FIG. 6. Among the different pathways evaluated, p38 MAPK was shown to be a major pathway responsible for the inhibitory action of pterostilbene on the synthesis of iNOS and COX-2. This was further confirmed by the inhibitory effect of pterostilbene on downstream targets of p38, namely ATF2 and Elk-1.

ATF2 is a subunit of the AP-1 complex and binds to the CRE promoter sequence on iNOS and COX-2 and Elk-1 belongs to the ETS transcription factor and binds to the ETS DNA-binding domain on the promoter sequence of inflammatory genes. In human iNOS gene expression, p38 activation is known to be associated with AP-1 binding to the iNOS promoter, suggesting that the effects of pterostilbene may be mediated by p38-AP-1 signaling. Further studies are required to understand the details of the action of pterostilbene on the p38-AP-1 signaling pathway.

The data presented in the instant application indicate that pterostilbene and pterostilbene analogs possess anti-proliferative and anti-inflammatory action in HT-29 colon cancer cells. Overall, pterostilbene is a promising compound with great potential as an anti-inflammatory drug and as an inhibitor of colon carcinogenesis.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A chemotherapeutic compound having a structure according to Formula I:

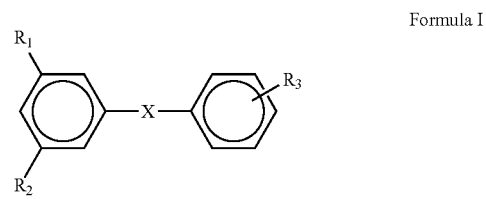

Formula I wherein X is selected from the group consisting of cis and trans ethylenyl;

$R_1$ and $R_2$ are independently selected from the group consisting of $C_1$-$C_3$ alkyls and $OR_4$, wherein $R_4$ is selected from the group consisting of hydrogen and $C_1$-$C_3$ alkyls; and $R_3$ is selected from the group consisting of halogens, glucose, $C_1$-$C_3$ alkyls, $NO_2$, $H_2PO_4$, $SO_2R_4$, $SR_4$, $COOR_4$, $COR_4$, $NR_5R_6$ and $COR_7$, wherein $R_4$, $R_5$, and $R_6$ are independently selected from the group consisting of hydrogen and $C_1$-$C_3$ alkyls; and $R_7$ is $NR_8R_9$, wherein $R_8$ and $R_9$ are independently selected from the group consisting of hydrogen and $C_1$-$C_3$ alkyls;

with the proviso that X, $R_1$, $R_2$ and $R_3$ may not be selected so that formula I is resveratrol or pterostilbene.

2. The compound of claim 1, wherein at least one of $R_1$, $R_2$ or $R_3$ is a $C_1$-$C_3$ alkyl or alkoxy substituted with OH, methyl or one to three halogens.

3. The compound of claim 1, wherein $R_3$ is SH or trifluoromethyl.

4. The compound of claim 1, wherein $R_3$ is F, Cl or Br.

5. The compound of claim 1, wherein $R_3$ is glucose.

6. The compound of claim 1, characterized by having a structure according to Formula II:

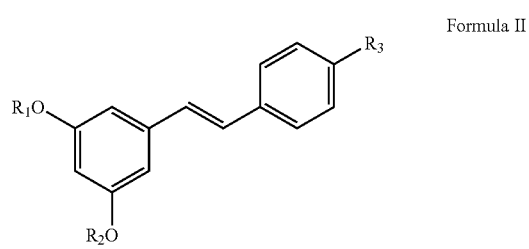

Formula II wherein $R_1$ and $R_2$ are independently selected from the group consisting of hydrogen and $C_1$-$C_3$ alkyls; and $R_3$ is selected from the group consisting of hydrogen, fluorine, chlorine, bromine, glucose, $C_1$-$C_3$ alkyls, $H_2PO_4$, $NO_2$, $NH_2$, SH and $COOR_4$, wherein $R_4$ is selected from the group consisting of hydrogen, and $C_1$-$C_3$ alkyls; or the compound has a structure according to Formula III

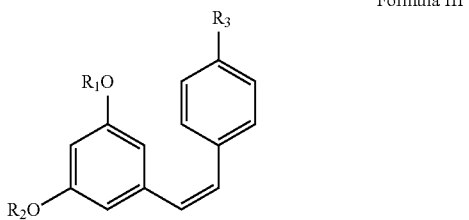

Formula III wherein $R_1$ and $R_2$ are independently selected from the group consisting of hydrogen and $C_1$-$C_3$ alkyls; and
$R_3$ is selected from the group consisting of hydrogen, fluorine, chlorine, bromine, $C_1$-$C_3$ alkyls, $NO_2$, $NH_2$, $SR_4$ and $COOR_4$, wherein $R_4$ is selected from the group consisting of hydrogen, and $C_1$-$C_3$ alkyls.

7. The compound of claim 6, wherein $R_1$=$R_2$=$CH_3$.

8. The compound of claim 7, wherein:
a) the compound has a structure according to Formula III, and $R_3$ is selected from the group consisting of $NO_2$, $SR_4$, $COOR_4$, and $NH_2$, wherein $R_4$ is a $C_1$-$C_3$ alkyl; or
b) the compound has a structure according to Formula II and $R_3$ is selected from the group consisting of $NO_2$, $SR_4$ and $NH_2$, wherein $R_4$ is a $C_1$-$C_3$ alkyl.

9. The compound of claim 8, wherein
a) the compound has a structure according to Formula III, and $R_3$ is selected from the group consisting of $NO_2$, $COOCH_3$, and $NH_2$; or
b) the compound has a structure according to Formula II and $R_3$ is $NH_2$.

10. The compound of claim 9, wherein:
a) the compound has a structure of Formula III, and $R_3$ is $COOR_4$, wherein $R_4$ is $CH_3$; or
b) the compound has a structure of Formula II, and $R_3$ is $NH_2$.

11. A chemotherapeutic compound according to claim 1 selected from the group consisting of (E)-1,3-dimethoxy-5-(4-nitrostyryl)benzene, (Z)-1,3-dimethoxy-5-(4-nitro-styryl)benzene, (E)-4-(3,5-dimethoxystyryl)aniline, (Z)-4-(3,5-dimethoxystyryl)aniline, (E)-methyl-4-(3,5-dimethoxystyryl)benzoate, (Z)-methyl 4-(3,5-dimethoxystyryl)benzoate, (E)-4-(3,5-dimethoxystyryl)benzoic acid, and (Z)-4-(3,5-dimethoxystyryl)benzoic acid.

12. A chemotherapeutic compound according to claim 1 selected from the group consisting of (E)-1,3-dimethoxy-5-(4-nitrostyryl)benzene, (Z)-1,3-dimethoxy-5-(4-nitro-styryl)benzene, (E)-4-(3,5-dimethoxystyryl)aniline, (Z)-4-(3,5-dimethoxystyryl)aniline, and (Z)-methyl-4-(3,5-dimethoxystyryl)benzoate.

13. A chemotherapeutic compound according to claim 1 selected from the group consisting of (E)-4-(3,5-dimethoxystyryl)aniline, and (Z)-methyl 4-(3,5-dimethoxystyryl)benzoate.

14. A method of treating colon inflammation in a subject in need thereof comprising administering to the subject an oral composition comprising a pharmaceutically acceptable carrier and a plant extract comprising pterostilbene.

15. The method of claim 14, wherein the pharmaceutically acceptable carrier comprises a gastro-resistant protective compound coated on said plant extract.

16. The method of claim 15, wherein said protective compound is applied in a manner to inhibit the substantial absorption of said plant extract into the gastrointestinal tract of the subject upstream of the small intestine.

17. A method of treating colon cancer or colon inflammation in a subject in need thereof comprising administering to said subject an effective amount of a compound according to claim 1.

18. A pharmaceutical composition comprising a pharmaceutically acceptable carrier and a compound according to claim 1.

\* \* \* \* \*

UNITED STATES PATENT AND TRADEMARK OFFICE
CERTIFICATE OF CORRECTION

Page 1 of 1

PATENT NO. : 8,426,369 B2
APPLICATION NO. : 12/518271
DATED : April 23, 2013
INVENTOR(S) : Agnes M. Rimando et al.

It is certified that error appears in the above-identified patent and that said Letters Patent is hereby corrected as shown below:

In the Specification

Column 1, Line 16, delete:
The research of the subject matter of the instant application was supported by NIH grant NIH/NCI K22 CA99990.
And insert:
--This invention was made with government support under grant number CA099990 awarded by the National Institutes of Health. The government has certain rights in the invention.--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*